(12) United States Patent
Tsuyama et al.

(10) Patent No.: US 10,270,044 B2
(45) Date of Patent: Apr. 23, 2019

(54) COATING SOLUTION FOR NON-LIGHT-EMITTING ORGANIC SEMICONDUCTOR DEVICE, ORGANIC TRANSISTOR, COMPOUND, ORGANIC SEMICONDUCTOR MATERIAL FOR NON-LIGHT-EMITTING ORGANIC SEMICONDUCTOR DEVICE, MATERIAL FOR ORGANIC TRANSISTOR, METHOD FOR MANUFACTURING ORGANIC TRANSISTOR, AND METHOD FOR MANUFACTURING ORGANIC SEMICONDUCTOR FILM

(71) Applicants: FUJIFILM Corporation, Tokyo (JP); The University of Tokyo, Tokyo (JP)

(72) Inventors: Hiroaki Tsuyama, Kanagawa (JP); Kimiatsu Nomura, Kanagawa (JP); Yoshihisa Usami, Kanagawa (JP); Masatoshi Yumoto, Kanagawa (JP); Tetsu Kitamura, Kanagawa (JP); Masashi Koyanagi, Kanagawa (JP); Tetsuya Watanabe, Kanagawa (JP); Toshihiro Okamoto, Tokyo (JP); Junichi Takeya, Tokyo (JP)

(73) Assignees: FUJIFILM Corporation, Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 16/180,118

(22) Filed: Nov. 5, 2018

(65) Prior Publication Data

US 2019/0074452 A1    Mar. 7, 2019

Related U.S. Application Data

(60) Division of application No. 15/943,968, filed on Apr. 3, 2018, which is a division of application No. 15/274,016, filed on Sep. 23, 2016, now Pat. No. 10,115,911, which is a continuation of application No. PCT/JP2015/059298, filed on Mar. 26, 2015.

(30) Foreign Application Priority Data

Mar. 26, 2014 (JP) ................................. 2014-063112
Mar. 12, 2015 (JP) ................................. 2015-049035

(51) Int. Cl.
| | |
|---|---|
| *C07D 495/14* | (2006.01) |
| *C09B 57/00* | (2006.01) |
| *C09D 5/24* | (2006.01) |
| *H01L 51/00* | (2006.01) |
| *H01L 51/05* | (2006.01) |

(52) U.S. Cl.
CPC ........ *H01L 51/0074* (2013.01); *C07D 495/14* (2013.01); *C09B 57/00* (2013.01); *C09D 5/24* (2013.01); *H01L 51/0007* (2013.01); *H01L 51/0558* (2013.01); *Y02E 10/549* (2013.01); *Y02P 70/521* (2015.11)

(58) Field of Classification Search
CPC ........ C07D 495/14; C09B 57/00; C09D 5/24; Y02P 70/521; Y02E 10/549
See application file for complete search history.

(56) References Cited

FOREIGN PATENT DOCUMENTS

| | | |
|---|---|---|
| CN | 102206225 A | 10/2011 |
| EP | 2 671 880 A1 | 12/2013 |
| JP | 2007-294721 A | 11/2007 |
| JP | 2009-302463 A | 12/2009 |
| JP | 2010-177642 A | 8/2010 |
| JP | 2013-77799 A | 4/2013 |
| JP | 2013-235903 A | 11/2013 |
| WO | 2011/126225 A1 | 10/2011 |
| WO | 2011/040155 A1 | 2/2013 |
| WO | 2014/034392 A1 | 3/2014 |
| WO | 2014/034393 A1 | 3/2014 |

OTHER PUBLICATIONS

International Search Report and Written Opinion issued in PCT/JP2015/059298; dated Jun. 30, 2015.
Wex et al.; End-capping of conjugated thiophene-benzene aromatic systems; Tehtahedron; Elsevier Science Publishers; Amsterdam, NL; vol. 66; No. 45; Nov. 6, 2010; pp. 8778-8784.
Holiday et al.; Advances in Charge Carrier Mobilities of Semiconducting Polymers Used in Organic Transistors; Chemistry of Materials; 2014; pp. 647-663.
Wex et al.; Synthesis of the anti and syn Isomers of Thieno[f,f']bis[1]benzothiophene. Comparison of the Optical and Electrochemical Properties of the anti and syn Isomers; J. Org. Chem.; 2005; pp. 4502-4505.

(Continued)

*Primary Examiner* — Timothy R Rozof
(74) *Attorney, Agent, or Firm* — Studebaker & Brackett PC

(57) ABSTRACT

Provided are a coating solution for a non-light-emitting organic semiconductor device having high carrier mobility that contains a compound represented by Formula (2) and a solvent having a boiling point of equal to or higher than 100° C., an organic transistor, a compound, an organic semiconductor material for a non-light-emitting organic semiconductor device, a material for an organic transistor, a method for manufacturing an organic transistor, and a method for manufacturing an organic semiconductor film.

Formula (2)

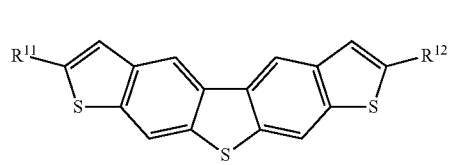

(In Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with a halogen atom.)

2 Claims, 5 Drawing Sheets

(56) References Cited

OTHER PUBLICATIONS

International Preliminary Report on Patentability (Chapter I) and Translation of Written Opinion of the International Searching Authority; PCT/JP2015/059298 dated Sep. 27, 2016.

An Office Action; "Notification of Reasons for Refusal," issued by the Japanese Patent Office dated Jan. 31, 2017, which corresponds to Japanese Patent Application No. 2015-049035 and is related to U.S. Appl. No. 15/274,016; with English language translation.

Extended European Search Report issued by the European Patent Office dated Feb. 27, 2017, which corresponds to European Patent Application No. 15769753.3-1555 and is related to U.S. Appl. No. 15/274,016; 6pp.

Wex et al.; Efficient Isoner-Pure Synthesis of a Benzo[b]thiophene Analogue of Pentacene; Journal of Organic Chemistry; vol. 69, No. 6; Mar. 2004; pp. 2197-2199.

Zhang et al.; Charge transport propertied in a series of five-ring-fused thienoacenes: A quantum chemistry and molecular mechanic study; Organic Electronics, Elsevier; Amsterdam, NL; vol. 14; No. 2; Dec. 20, 2012; pp. 607-620.

Wex et al.; New organic semiconductors and their device performance as a function of thiophene orientation; Journal of Material Chemistry; 2006; vol. 16; No. 12; pp. 1121-1124.

An Office Action; "Notice of Reasons for Rejection," mailed by the Japanese Patent Office dated Aug. 15, 2017, which corresponds to Japanese Patent Application No. 2015-049035; with its English Machine Translation.

An Office Action issued by the Korean Patent Office dated Jan. 11, 2018, which corresponds to Korean Patent Application 10-2016-7026432 and is related to U.S. Appl. No. 15/274,016.

Sureshbabu et al.; 5 Eur. J. Org. Chem. 922-935 (2011) (CAS Abstract) (Year: 2011).

An Office Action issued by the Chinese Patent Office (SIPO) dated Oct. 23, 2018, which corresponds to Chinese Patent Application No. 201580015681.1 and is related to U.S. Appl. No. 16/180,118; with English language translation.

An Office Action; "Notification of Reasons for Refusal," issued by the Japanese Patent Office dated Dec. 18, 2018, which corresponds to Japanese Patent Application No. 2017-219041 and is related to U.S. Appl. No. 16/180,118; with English language translation.

COATING SOLUTION FOR NON-LIGHT-EMITTING ORGANIC SEMICONDUCTOR DEVICE, ORGANIC TRANSISTOR, COMPOUND, ORGANIC SEMICONDUCTOR MATERIAL FOR NON-LIGHT-EMITTING ORGANIC SEMICONDUCTOR DEVICE, MATERIAL FOR ORGANIC TRANSISTOR, METHOD FOR MANUFACTURING ORGANIC TRANSISTOR, AND METHOD FOR MANUFACTURING ORGANIC SEMICONDUCTOR FILM

CROSS-REFERENCE TO RELATED APPLICATIONS

This application is a Divisional Application of U.S. patent application Ser. No. 15/943,968 filed Apr. 3, 2018, which is Divisional Application of U.S. patent application Ser. No. 15/274,016 filed Sep. 23, 2016, which is a Continuation of PCT International Application No. PCT/JP2015/059298, filed on Mar. 26, 2015, which claims priority under 35 U.S.C. Section 119(a) to Japanese Patent Application No. 2014-063112 filed on Mar. 26, 2014 and Japanese Patent Application No. 2015-049035 filed on Mar. 12, 2015. Each of the above applications is hereby expressly incorporated by reference, in its entirety, into the present application.

BACKGROUND OF THE INVENTION

1. Field of the Invention

The present invention relates to a coating solution for a non-light-emitting organic semiconductor device, an organic transistor, a compound, an organic semiconductor material for a non-light-emitting organic semiconductor device, a material for an organic transistor, a method for manufacturing an organic transistor, and a method for manufacturing an organic semiconductor film. Specifically, the present invention relates to a compound having a thieno[3,2-f:4,5-f']bis[1]benzothiophene skeletal structure and to a coating solution for a non-light-emitting organic semiconductor device, an organic transistor, an organic semiconductor material for a non-light-emitting organic semiconductor device, a material for an organic transistor, a method for manufacturing an organic transistor, and a method for manufacturing an organic semiconductor film which use a compound having a thieno[3,2-f:4,5-f']bis[1]benzothiophene skeletal structure.

2. Description of the Related Art

Devices using organic semiconductor materials are drawing great attention because they are expected to be superior in various aspects to devices using inorganic semiconductor materials of the related art such as silicon. Examples of the devices using organic semiconductor materials include a photoelectric conversion element such as an organic thin-film solar cell or a solid-state imaging element using organic semiconductor materials as photoelectric conversion materials, an organic transistor (referred to as an organic thin-film transistor in some cases) having non-light-emitting properties (in the present specification, "non-light-emitting" refers to properties by which a luminous efficiency of equal to or less than 1 lm/W is obtained in a case where electric currents are applied to a device at a current density of 0.1 mW/cm² at room temperature in the atmosphere; non-light-emitting organic semiconductor devices mean organic semiconductor devices excluding light-emitting organic semiconductor devices such as organic electroluminescence elements), and the like. Compared to the devices using inorganic semiconductor materials, the devices using organic semiconductor materials are likely to make it possible to prepare large area elements at lower temperature and lower costs. Furthermore, the characteristics of the materials can be easily changed by varying the molecular structure thereof. Therefore, the materials show a wide variation and can realize functions or elements that cannot be obtained by inorganic semiconductor materials.

Regarding organic transistor materials, the use of compounds having a fused ring in a semiconductor active layer is examined so as to improve carrier mobility and to improve transistor performances.

As materials for an organic transistor, compounds having a thieno[3,2-f:4,5-f']bis[1]benzothiophene (hereinafter, referred to as TBBT as well) structure on the inside thereof are known. For example, Tetrahedron 66 (2010) 8778-8784 discloses a method for synthesizing a compound C6-TBBT or C12-TBBT obtained by substituting thieno[3,2-f:4,5-f'] bis[1]benzothiophene with an alkyl group having 6 carbon atoms or an alkyl group having 12 carbon atoms respectively, and discloses absorption/emission spectra and cyclic voltammetry (CV) as physical properties of the compound. Tetrahedron 66 (2010) 8778-8784 describes the application of the compound to an organic transistor in the introduction part of the document. However, the document merely describes the measurement of the absorption/emission spectra or the oxidation-reduction potential of the solution, but does not describe the formation of a film, the physical properties of the film, the evaluation of organic transistor characteristics such as carrier mobility, and the like.

SUMMARY OF THE INVENTION

Under the circumstances described above, the inventors of the present invention examined organic transistors using the compound described in Tetrahedron 66 (2010) 8778-8784. As a result, the inventors found that, even if a coating film is formed using a solution, which is for measuring the oxidation-reduction potential or absorption/emission spectra by using the compound having a TBBT structure on the inside thereof, as it is, carrier mobility cannot be increased. The inventors found that, accordingly, carrier mobility needs to be further improved.

An object of the present invention is to provide an organic transistor having high carrier mobility.

As a result of conducting intensive examination for achieving the above object, the inventors obtained knowledge that, by substituting a skeleton having a thieno[3,2-f: 4,5-f']bis[1]benzothiophene (hereinafter, referred to as TBBT as well) structure on the inside thereof with a specific substituent, an organic transistor having high carrier mobility can be obtained, and accomplished the present invention.

The present invention as specific means for achieving the above object has the following constitution.

[1] A coating solution for a non-light-emitting organic semiconductor device comprising a compound represented by the following Formula (2) and a solvent having a boiling point of equal to or higher than 100° C.;

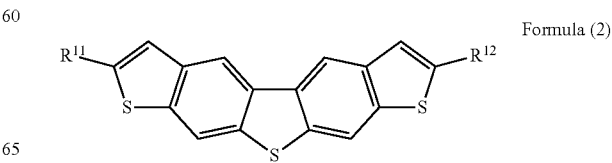

Formula (2)

in Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with a halogen atom.

[2] The coating solution for a non-light-emitting organic semiconductor device described in [1], in which the compound represented by Formula (2) preferably satisfies the following condition A, B, C, or D;

condition A: in Formula (2), $R^{11}$ and $R^{12}$ each independently have 3 to 30 carbon atoms in total and represent an unsubstituted linear alkyl group having an even number of carbon atoms within a range of 8 to 10 carbon atoms, an unsubstituted linear alkyl group having an odd number of carbon atoms within a range of 3 to 15 carbon atoms, a substituted linear alkyl group having 3 to 15 carbon atoms, or a substituted or unsubstituted branched alkyl group having 3 to 18 carbon atoms, and an aromatic portion in Formula (2) may be substituted with a halogen atom;

condition B: in Formula (2), $R^{11}$ and $R^{12}$ each independently have 3 to 30 carbon atoms in total and represent an unsubstituted linear alkyl group having an even number of carbon atoms within a range of 2 to 4 carbon atoms;

condition C: in Formula (2), $R^{11}$ and $R^{12}$ each independently have 3 to 30 carbon atoms in total and represent a substituted alkyl group having 1 or 2 carbon atoms;

condition D: in Formula (2), $R^{11}$ and $R^{12}$ each independently have 3 to 30 carbon atoms in total, and $R^{11}$ and $R^{12}$ have different structures.

[3] The coating solution for a non-light-emitting organic semiconductor device described in [2], in which the compound represented by Formula (2) preferably satisfies the following condition A;

condition A: in Formula (2), $R^{11}$ and $R^{12}$ each independently have 3 to 30 carbon atoms in total and represent an unsubstituted linear alkyl group having an even number of carbon atoms within a range of 8 to 10 carbon atoms, an unsubstituted linear alkyl group having an odd number of carbon atoms within a range of 3 to 15 carbon atoms, a substituted linear alkyl group having 3 to 15 carbon atoms, or a substituted or unsubstituted branched alkyl group having 3 to 18 carbon atoms, and an aromatic portion in Formula (2) may be substituted with a halogen atom.

[4] The coating solution for a non-light-emitting organic semiconductor device described in [3], in which in Formula (2), $R^{11}$ and $R^{12}$ each preferably independently have 3 to 30 carbon atoms in total and represent an unsubstituted linear alkyl group having an even number of carbon atoms within a range of 8 to 10 carbon atoms or an unsubstituted linear alkyl group having an odd number of carbon atoms within a range of 3 to 15 carbon atoms, and an aromatic portion in Formula (2) may be substituted with a halogen atom.

[5] The coating solution for a non-light-emitting organic semiconductor device described in [3] or [4], in which in Formula (2), $R^{11}$ and $R^{12}$ each preferably independently have 3 to 30 carbon atoms in total and represent a linear alkyl group having 3 to 15 carbon atoms substituted with a substituent through an ether structure or an ester bond.

[6] The coating solution for a non-light-emitting organic semiconductor device described in [2], in which the compound represented by Formula (2) preferably satisfies the following condition B;

condition B: in Formula (2), $R^{11}$ and $R^{12}$ each independently have 3 to 30 carbon atoms in total and represent an unsubstituted linear alkyl group having an even number of carbon atoms within a range of 2 to 4 carbon atoms.

[7] The coating solution for a non-light-emitting organic semiconductor device described in [2], in which the compound represented by Formula (2) preferably satisfies the following condition C;

condition C: in Formula (2), $R^{11}$ and $R^{12}$ each independently have 3 to 30 carbon atoms in total and represent a substituted alkyl group having 1 or 2 carbon atoms.

[8] The coating solution for a non-light-emitting organic semiconductor device described in [7], in which in Formula (2), $R^{11}$ and $R^{12}$ each preferably independently have 3 to 30 carbon atoms in total and represent an alkyl group having 1 or 2 carbon atoms substituted with a substituent through an ether structure or an ester bond.

[9] The coating solution for a non-light-emitting organic semiconductor device described in [2], in which the compound represented by Formula (2) preferably satisfies the following condition D;

condition D: in Formula (2), $R^{11}$ and $R^{12}$ each independently have 3 to 30 carbon atoms in total, and $R^{11}$ and $R^{12}$ have different structures.

[10] The coating solution for a non-light-emitting organic semiconductor device described in [9], in which in Formula (2), $R^{11}$ and $R^{12}$ each preferably independently have 3 to 30 carbon atoms in total, $R^{11}$ preferably represents an unsubstituted linear alkyl group, and $R^{12}$ preferably represents a substituted or unsubstituted linear or branched alkyl group different from $R^{11}$.

[11] The coating solution for a non-light-emitting organic semiconductor device described in [10], in which in Formula (2), $R^{11}$ and $R^{12}$ each preferably independently have 3 to 30 carbon atoms in total and represent an unsubstituted linear alkyl group, and $R^{11}$ and $R^{12}$ preferably have different structures.

[12] An organic transistor comprising a compound represented by the following Formula (2) in a semiconductor active layer;

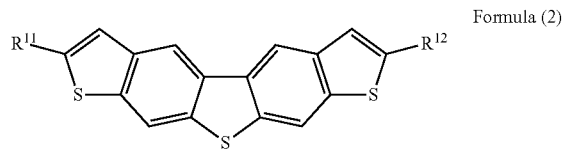

Formula (2)

in Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with a halogen atom.

[13] The organic transistor described in [12], in which the compound represented by Formula (2) preferably satisfies the following condition A;

condition A: in Formula (2), $R^{11}$ and $R^{12}$ each independently have 3 to 30 carbon atoms in total and represent an unsubstituted linear alkyl group having an even number of carbon atoms within a range of 8 to 10 carbon atoms, an unsubstituted linear alkyl group having an odd number of carbon atoms within a range of 3 to 15 carbon atoms, a substituted linear alkyl group having 3 to 15 carbon atoms, or a substituted or unsubstituted branched alkyl group having 3 to 18 carbon atoms, and an aromatic portion in Formula (2) may be substituted with a halogen atom.

[14] A compound which is represented by the following Formula (2) and satisfies the following condition A, B, C, or D;

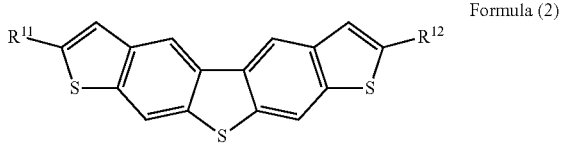

Formula (2)

in Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with an halogen atom;

condition A: in Formula (2), $R^{11}$ and $R^{12}$ each independently have 3 to 30 carbon atoms in total and represent an unsubstituted linear alkyl group having an even number of carbon atoms within a range of 8 to 10 carbon atoms, an unsubstituted linear alkyl group having an odd number of carbon atoms within a range of 3 to 15 carbon atoms, a substituted linear alkyl group having 3 to 15 carbon atoms, or a substituted or unsubstituted branched alkyl group having 3 to 18 carbon atoms, and an aromatic portion in Formula (2) may be substituted with a halogen atom;

condition B: in Formula (2), $R^{11}$ and $R^{12}$ each independently have 3 to 30 carbon atoms in total and represent an unsubstituted linear alkyl group having an even number of carbon atoms within a range of 2 to 4 carbon atoms;

condition C: in Formula (2), $R^{11}$ and $R^{12}$ each independently have 3 to 30 carbon atoms in total and represent a substituted alkyl group having 1 or 2 carbon atoms;

condition D: in Formula (2), $R^{11}$ and $R^{12}$ each independently have 3 to 30 carbon atoms in total, and $R^{11}$ and $R^{12}$ have different structures.

[15] The compound described in [14], in which the compound represented by Formula (2) preferably satisfies the following condition A;

condition A: in Formula (2), $R^{11}$ and $R^{12}$ each independently have 3 to 30 carbon atoms in total and represent an unsubstituted linear alkyl group having an even number of carbon atoms within a range of 8 to 10 carbon atoms, an unsubstituted linear alkyl group having an odd number of carbon atoms within a range of 3 to 15 carbon atoms, a substituted linear alkyl group having 3 to 15 carbon atoms, or a substituted or unsubstituted branched alkyl group having 3 to 18 carbon atoms, and an aromatic portion in Formula (2) may be substituted with a halogen atom.

[16] An organic semiconductor material for a non-light-emitting organic semiconductor device containing the compound described in [14] or [15].

[17] A material for an organic transistor containing the compound described in [14] or [15].

[18] A coating solution for a non-light-emitting organic semiconductor device containing the compound described in [14] or [15].

[19] An organic transistor containing the compound described in [14] or [15] in a semiconductor active layer.

[20] A method for manufacturing an organic transistor, comprising a step of preparing a semiconductor active layer by coating a substrate with the coating solution for a non-light-emitting organic semiconductor device described in any one of [1] to [11] and [18] and drying the coating solution.

[21] A method for manufacturing an organic semiconductor film, in which in a state where a distance between a substrate A and a member B not being fixed to the substrate A is kept constant or in a state where the substrate A and the member B are caused to remain in contact with each other, a coating solution, which contains a compound represented by the following Formula (2) and a solvent having a boiling point of equal to or higher than 100° C., is dropped onto a portion within the surface of the substrate A such that the coating solution contacts both of the substrate A and the member B, and the dropped coating solution is slowly dried, such that crystals of the compound represented by Formula (2) are precipitated and a semiconductor active layer is formed;

here, as long as the distance between the substrate A and the member B is kept constant or as long as the substrate A and the member B are caused to remain in contact with each other, the positional relationship between the substrate A and the member B may be maintained or changed when the coating solution is dropped or dried;

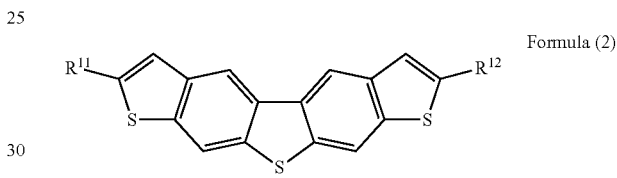

Formula (2)

in Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with a halogen atom.

[22] A method for manufacturing an organic semiconductor film, in which in a state where a distance between a substrate A and a member B not being fixed to the substrate A is kept constant or in a state where the substrate A and the member B are caused to remain in contact with each other, a coating solution, which is prepared by dissolving the compound described in [14] or [15] in a solvent, is dropped onto a portion within the surface of the substrate A such that the coating solution contacts both of the substrate A and the member B, and the dropped coating solution is slowly dried, such that crystals of the compound described in [14] or [15] are precipitated and a semiconductor active layer is formed;

here, as long as the distance between the substrate A and the member B is kept constant or as long as the substrate A and the member B are caused to remain in contact with each other, the positional relationship between the substrate A and the member B may be maintained or changed when the coating solution is dropped or dried.

The coating solution for a non-light-emitting organic semiconductor device described in any one of [1] to [11], in which the solvent having a boiling point of equal to or higher than 100° C. is preferably a non-halogen-based solvent.

The coating solution for a non-light-emitting organic semiconductor device described in any one of [1] to [11] and [18], in which the concentration of the compound represented by Formula (2) is preferably equal to or greater than 0.4% by mass.

The coating solution for a non-light-emitting organic semiconductor device described in any one of [1] to [11] and

[18] that preferably contains two or more kinds of compound represented by Formula (2).

The coating solution for a non-light-emitting organic semiconductor device described in any one of [1] to [11] and [18] that preferably has a viscosity of equal to or higher than 10 mPa·s.

The coating solution for a non-light-emitting organic semiconductor device described in any one of [1] to [11] and [18] that preferably contains a polymer.

A coating film comprising a compound represented by the following Formula (2);

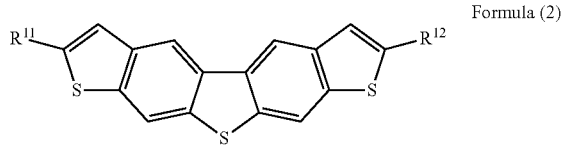

Formula (2)

in Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with a halogen atom.

A coating film comprising the compound described in [14] or [15].

According to the present invention, it is possible to provide an organic transistor having high carrier mobility.

BRIEF DESCRIPTION OF THE DRAWINGS

FIGS. 3A to 3C are schematic views showing an aspect in which in a state where a distance between a substrate A and a member B not being fixed to the substrate A is kept constant, a coating solution is dropped onto a portion within the surface of the substrate A such that the coating solution contacts both of the substrate A and the member B, and the dropped coating solution is slowly dried in a state where the positional relationship between the substrate A and the member B is maintained.

FIGS. 4A to 4C are schematic views showing another example of the method for manufacturing an organic semiconductor film of the present invention. Specifically, FIGS. 4A to 4C are schematic views showing an aspect in which in a state where the substrate A and the member B remain in contact with each other, a coating solution is dropped onto a portion within the surface of the substrate A such that the coating solution contacts both of the substrate A and the member B, and the dropped coating solution is slowly dried in a state where the positional relationship between the substrate A and the member B is maintained.

5A to 5C are schematic views showing an aspect in which in a state where the substrate A and the member B remain in contact with each other, a coating solution is dropped onto a portion within the surface of the substrate A such that the coating solution contacts both of the substrate A and the member B, and the dropped coating solution is slowly dried by changing the positional relationship between the substrate A and the member B.

Figure 6:
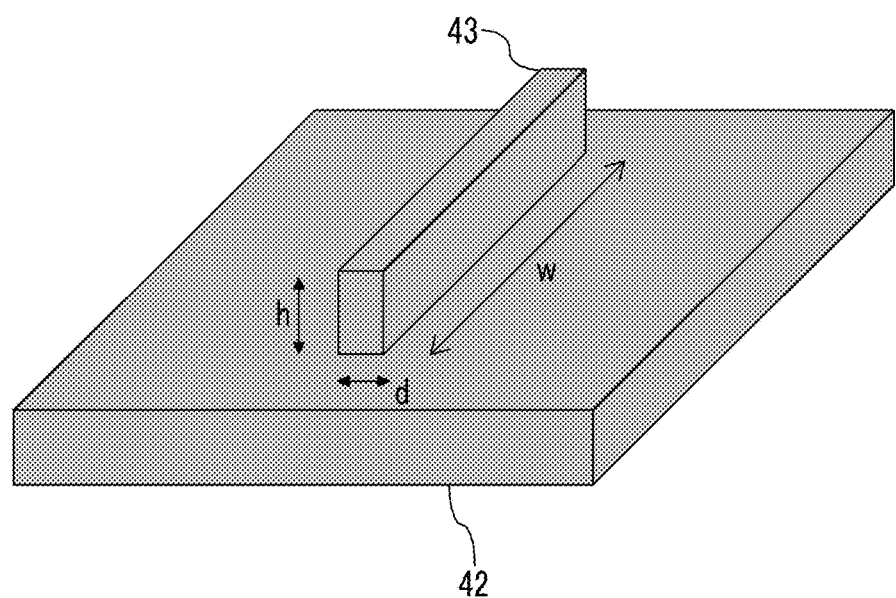

FIG. 6 is a schematic view showing an example of the substrate A and the member B used in the method for manufacturing an organic semiconductor film of the present invention.

DESCRIPTION OF THE PREFERRED EMBODIMENTS

Hereinafter, the present invention will be specifically described. The constituents described below will be explained based on representative embodiments or specific examples, but the present invention is not limited to the embodiments. In the present specification, a range of numerical values described using "to" means a range including the numerical values listed before and after "to" as a lower limit and an upper limit respectively.

In the present invention, unless otherwise specified, a hydrogen atom used in the description of each formula represents a hydrogen atom including an isotope (deuterium atom or the like). Furthermore, an atom constituting a substituent represents an atom including an isotope thereof.

[Coating Solution for Non-Light-Emitting Organic Semiconductor Device/Organic Transistor/Compound]

A first aspect of a coating solution for a non-light-emitting organic semiconductor device of the present invention contains a compound represented by the following Formula (2) and a solvent having a boiling point of equal to or higher than 100° C.;

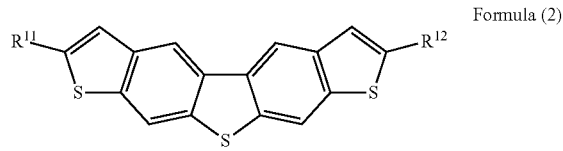

Formula (2)

in Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with a halogen atom.

A second aspect of the coating solution for a non-light-emitting organic semiconductor device of the present invention is a coating solution for a non-light-emitting organic semiconductor device containing a compound of the present invention that will be described later.

A first aspect of an organic transistor of the present invention contains a compound represented by the following Formula (2) in a semiconductor active layer.

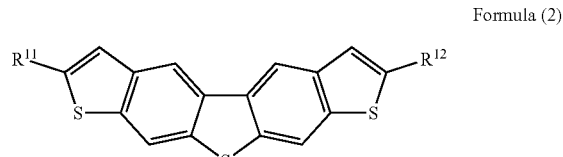

Formula (2)

In Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with a halogen atom.

In the first aspect of the organic transistor of the present invention, the semiconductor layer may contain the compound represented by Formula (2) and a solvent having a boiling point of equal to or higher than 100° C. or may contain the compound represented by Formula (2) (here, a compound satisfying a condition A, B, C, or D is excluded) and a solvent having a boiling point of equal to or higher than 100° C.

Furthermore, in the first aspect of the organic transistor of the present invention, the semiconductor active layer is preferably manufactured using a solution containing the compound represented by Formula (2) and a solvent having a boiling point of equal to or higher than 100° C., and is more preferably manufactured using a solution containing the compound represented by Formula (2) (here, a compound satisfying a condition A, B, C, or D is excluded) and a solvent having a boiling point of equal to or higher than 100° C.

A second aspect of the organic transistor of the present invention is an organic transistor containing a compound of the present invention that will be described later in a semiconductor active layer.

By adopting the aforementioned constitution, the organic transistor of the present invention exhibits high carrier mobility. In addition, the coating solution for a non-light-emitting organic semiconductor device of the present invention can provide the organic transistor of the present invention having high carrier mobility. Presumably, though the presumption is not restricted by any theory, in the first aspect, if the compound represented by Formula (2) having a specific substituent is used, an organic transistor having high carrier mobility is obtained even though the reason has not yet been clarified in detail (the improvement of solubility or the like is considered to exert an influence). In the first aspect, in order to rapidly dry the solution at the time of forming a film, it is preferable to use a solvent having a higher boiling point. Particularly, in a case where the compound represented by Formula (2) (here, a compound satisfying a condition A, B, C, or D is excluded) is used in the semiconductor active layer, an organic transistor having high carrier mobility is more easily obtained. Furthermore, presumably, in the second aspect, if a compound of the present invention having a specific substituent that will be described later is used, an organic transistor having high carrier mobility is obtained, even though the reason has not yet been clarified in detail (the improvement of solubility or the like is considered to exert an influence).

It cannot be said that being useful as a material of an organic electroluminescence (EL) element means being useful as a semiconductor material for an organic transistor. This is because the characteristics required for an organic compound vary between an organic EL element and an organic transistor. A mobility of about $10^{-3}$ cm$^2$/Vs is enough for driving an organic EL element, and for improving organic EL characteristics, it is more important to improve luminous efficiency than to improve charge transport properties. Therefore, an element having high luminous efficiency and resulting in uniform in-plane luminescence is required. Generally, organic compounds having high crystallinity (high mobility) cause luminescence defectiveness such as non-uniform in-plane field intensity, non-uniform luminescence, and quenching of luminescence. Therefore, as materials for an organic EL element, those having low crystallinity but having high amorphousness (low mobility) are desirable. In contrast, in a semiconductor material for an organic transistor, extremely high mobility is desired. Accordingly, an organic compound showing highly ordered molecular arrangement and having high crystallinity is required. Furthermore, for the expression of high carrier mobility, a π-conjugate plane is preferably upright against a substrate.

First, the coating solution for a non-light-emitting organic semiconductor device of the present invention that can also be used as a coating solution in a method for manufacturing an organic semiconductor film of the present invention that will be described later will be explained.

Hereinafter, the first and second aspects of the coating solution for a non-light-emitting organic semiconductor device of the present invention will be comprehensively described.

<Compound Represented by Formula (2)>

The compound represented by the following Formula (2) will be described.

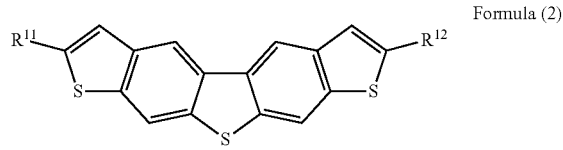

Formula (2)

In Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with a halogen atom.

Preferred aspects of the structure of the compound represented by Formula (2) will be described.

In Formula (2), the alkyl group represented by $R^{11}$ and $R^{12}$ is not particularly limited. The alkyl group is preferably an alkyl group having 1 to 30 carbon atoms and may be linear, branched, or cyclic. In Formula (2), the alkyl group represented by $R^{11}$ and $R^{12}$ has 3 to 30 carbon atoms in total. The alkyl group is more preferably an unsubstituted linear alkyl group having an even number of carbon atoms within a range of 8 to 10 carbon atoms, an unsubstituted linear alkyl group having an odd number of carbon atoms within a range of 3 to 15 carbon atoms, a substituted linear alkyl group having 3 to 15 carbon atoms, or a substituted or unsubstituted branched alkyl group having 3 to 18 carbon atoms. A particularly preferred range of the alkyl group represented by $R^{11}$ and $R^{12}$ is the same as the range in which a condition A, B, C, or D, which will be described later, is satisfied.

In Formula (2), the alkenyl group represented by $R^{11}$ and $R^{12}$ is not particularly limited. The alkenyl group is preferably an alkenyl group having 2 to 30 carbon atoms, more preferably an alkenyl group having 3 to 18 carbon atoms, and particularly preferably an alkenyl group having 5 to 13 carbon atoms.

In Formula (2), the alkynyl group represented by $R^{11}$ and $R^{12}$ is not particularly limited. The alkynyl group is preferably an alkynyl group having 2 to 30 carbon atoms, more preferably an alkynyl group having 3 to 18 carbon atoms, and particularly preferably an alkynyl group having 5 to 13 carbon atoms.

In Formula (2), the alkoxy group represented by $R^{11}$ and $R^{12}$ is not particularly limited. The alkoxy group is preferably an alkoxy group having 1 to 30 carbon atoms, more preferably an alkoxy group having 3 to 18 carbon atoms, and particularly preferably an alkoxy group having 5 to 13 carbon atoms.

In the compound represented by Formula (2), each of $R^{11}$ and $R^{12}$ is preferably an alkyl group.

In a case where the alkyl group, the alkenyl group, the alknyl group, or the alkoxy group represented by $R^{11}$ and $R^{12}$ in Formula (2) further has a substituent, the substituent is not particularly limited. Examples of the substituent include a halogen atom, an alkenyl group (including an ethenyl group, a 1-pentenyl group, a 1-heptanyl group, a cycloalkenyl group, a bicycloalkenyl group, and the like), an alkynyl group (including a 1-pentynyl group, a trimethylsilylethynyl group, a triethylsilylethynyl group, a tri-i-propylsilylethynyl group, a 2-p-propylphenylethynyl group, and the like), an aryl group (including an aryl group having 6 to 20 carbon atoms such as a phenyl group, a naphthyl group, a p-pentylphenyl group, a 3,4-dipentylphenyl group, a p-heptoxyphenyl group, a 3,4-diheptoxyphenyl group, and the like), a hetero ring group (may be referred to as a heterocyclic group as well, including a 2-hexylfuranyl group and the like), a cyano group, a hydroxyl group, a nitro group, an acyl group (including a hexanoyl group, a benzoyl group, and the like), an alkoxy group (including a butoxy group and the like), an aryloxy group (including a phenoxy group and the like), a silyloxy group, a heterocyclic oxy group, an acyloxy group, a carbamoyloxy group, an amino group (including an anilino group), an acylamino group, an aminocarbonylamino group (including a ureido group), alkoxy- and aryloxycarbonylamino groups, alkyl- and aryl sulfonylamino groups, a mercapto group, alkyl- and arylthio groups (including a methylthio group, an octylthio group, and the like), a heterocyclic thio group, a sulfamoyl group, a sulfo group, alkyl- and aryl sulfinyl groups, alkyl- and aryl sulfonyl groups, alkyloxy- and aryloxycarbonyl groups, a carbamoyl group, aryl- and heterocyclic azo group, an imido group, a phosphino group, a phosphinyl group, a phosphinyloxy group, a phosphinylamino group, a phosphono group, a silyl group (a ditrimethylsiloxy methylbutoxy group), a hydrazino group, a ureido group, a boronic acid group (—B(OH)$_2$), a phosphate group (—OPO(OH)$_2$), a sulfate group (—OSO$_3$H), and other known substituents. Among these, a halogen atom, an alkoxy group, an acyloxy group, and an alkyloxycarbonyl group are particularly preferable, and a halogen atom and an alkoxy group are most preferable.

These substituents may further have the substituents described above.

In the compound represented by Formula (2), an aromatic portion in Formula (2) may be substituted with a halogen atom, and as the halogen atom, a fluorine atom is preferable. The number of carbon atoms substituting the aromatic portion in Formula (2) is preferably 0 to 6, more preferably 0 to 4, particularly preferably 0 to 2, and more particularly preferably 0.

Even in a case where the aromatic portion in Formula (2) is substituted with a substituent other than a halogen atom, an organic transistor having high carrier mobility is obtained as in a case where the aromatic portion in Formula (2) is unsubstituted or substituted with a halogen atom, and functions such as high solubility can be imparted to the compound represented by Formula (2).

In the compound represented by Formula (2), even in a case where a thiophene ring portion in which $R^{11}$ or $R^{12}$ in Formula (2) is substituted is further substituted with a substituent other than $R^{11}$ and $R^{12}$, an organic transistor having high carrier mobility is obtained as in a case where the thiophene ring portion in which $R^{11}$ or $R^{12}$ is substituted is unsubstituted, and functions such as high solubility can be imparted to the compound represented by Formula (2).

(Compound of the Present Invention)

In the present invention, the compound represented by Formula (2) preferably satisfies the following condition A, B, C, or D;

condition A: in Formula (2), $R^{11}$ and $R^{12}$ each independently have 3 to 30 carbon atoms in total and represent an unsubstituted linear alkyl group having an even number of carbon atoms within a range of 8 to 10 carbon atoms, an unsubstituted linear alkyl group having an odd number of carbon atoms within a range of 3 to 15 carbon atoms, a substituted linear alkyl group having 3 to 15 carbon atoms, or a substituted or unsubstituted branched alkyl group having 3 to 18 carbon atoms, and an aromatic portion in Formula (2) may be substituted with a halogen atom;

condition B: in Formula (2), $R^{11}$ and $R^{12}$ each independently have 3 to 30 carbon atoms in total and represent an unsubstituted linear alkyl group having an even number of carbon atoms within a range of 2 to 4 carbon atoms;

condition C: in Formula (2), $R^{11}$ and $R^{12}$ each independently have 3 to 30 carbon atoms in total and represent a substituted alkyl group having 1 or 2 carbon atoms;

condition D: in Formula (2), $R^{11}$ and $R^{12}$ each independently have 3 to 30 carbon atoms in total, and $R^{11}$ and $R^{12}$ have different structures.

The compound satisfying the condition A, B, C, or D is a novel compound and referred to as a compound of the present invention. That is, the compound of the present invention is a compound which is represented by Formula (2) and satisfies the following conditions A, B, C, or D. In the organic transistor of the present invention, the compound of the present invention is contained in a semiconductor active layer which will be described later. That is, the compound of the present invention can be used as a material for an organic transistor.

Particularly, unlike the compound C6-TBBT or C12-TBBT, described in Tetrahedron 66 (2010) 8778-8784, obtained by substituting thieno[3,2-f:4,5-f']bis[1]benzothiophene with an alkyl group having 6 carbon atoms or an alkyl group having 12 carbon atoms respectively, the compound of the present invention further improves carrier mobility in the organic transistor of the present invention by being contained in the semiconductor active layer.

According to the inventors of the present invention, the reason is assumed to be as below, although the present invention is not restricted by any reason. By selecting a specific alkyl chain length or shape that the compound of the present invention may satisfy, an orbital overlap greatly occurs between molecules, and as a result, carrier mobility can be further improved in the organic transistor of the present invention.

Hereinafter, the conditions A, B, C, and D as preferred aspects of the compound represented by Formula (2) will be described.

(Condition A)

In the present invention, the compound represented by Formula (2) more preferably satisfies the following condition A;

condition A: in Formula (2), $R^{11}$ and $R^{12}$ each independently have 3 to 30 carbon atoms in total and represent an unsubstituted linear alkyl group having an even number of carbon atoms within a range of 8 to 10 carbon atoms, an unsubstituted linear alkyl group having an odd number of carbon atoms within a range of 3 to 15 carbon atoms, a substituted linear alkyl group having 3 to 15 carbon atoms, or a substituted or unsubstituted branched alkyl group having 3 to 18 carbon atoms, and an aromatic portion in Formula (2) may be substituted with a halogen atom.

The unsubstituted linear alkyl group having an even number of carbon atoms within a range of 8 to 10 carbon atoms that is represented by $R^{11}$ and $R^{12}$ is preferably a linear alkyl group having 8 or 10 carbon atoms, and particularly a linear alkyl group having 10 carbon atoms. The unsubstituted linear alkyl group is preferably a long-chain alkyl group that falls into the above range, and particularly preferably a long-chain linear alkyl group, because then the molecular linearity is improved, and hence carrier mobility can be improved.

The unsubstituted linear alkyl group having an odd number of carbon atoms within a range of 3 to 15 carbon atoms that is represented by $R^{11}$ and $R^{12}$ is preferably an unsubstituted linear alkyl group having an odd number of carbon atoms within a range of 5 to 15 carbon atoms, more preferably an unsubstituted linear alkyl group having an odd number of carbon atoms within a range of 7 to 13 carbon atoms, and particularly preferably an unsubstituted linear alkyl group having 9 or 11 carbon atoms.

Each of $R^{11}$ and $R^{12}$ is preferably a linear alkyl group, because then the molecular linearity is improved, and hence carrier mobility can be improved. In contrast, from the viewpoint of improving solubility in an organic solvent, each of $R^{11}$ and $R^{12}$ may be a branched alkyl group.

In a case where each of $R^{11}$ and $R^{12}$ is a substituted linear alkyl group having 3 to 15 carbon atoms or a substituted branched alkyl group having 3 to 18 carbon atoms, the substituent is not particularly limited. Examples of the substituent include a halogen atom, an alkenyl group (including an ethenyl group, a 1-pentenyl group, a 1-heptanyl group, a cycloalkenyl group, a bicycloalkenyl group, and the like), an alkynyl group (including a 1-pentynyl group, a trimethylsilylethynyl group, a triethylsilylethynyl group, a tri-i-propylsilylethynyl group, a 2-p-propylphenylethynyl group, and the like), an aryl group (including an aryl group having 6 to 20 carbon atoms such as a phenyl group, a naphthyl group, a p-pentylphenyl group, a 3,4-dipentylphenyl group, a p-heptoxyphenyl group, a 3,4-diheptoxyphenyl group, and the like), a hetero ring group (may be referred to as a heterocyclic group as well, including a 2-hexylfuranyl group and the like), a cyano group, a hydroxyl group, a nitro group, an acyl group (including a hexanoyl group, a benzoyl group, and the like), an alkoxy group (including a butoxy group and the like), an aryloxy group (including a phenoxy group and the like), a silyloxy group, a heterocyclic oxy group, an acyloxy group, a carbamoyloxy group, an amino group (including an anilino group), an acylamino group, an aminocarbonylamino group (including a ureido group), alkoxy- and aryloxycarbonylamino groups, alkyl- and aryl sulfonylamino groups, a mercapto group, alkyl- and arylthio groups (including a methylthio group, an octylthio group, and the like), a heterocyclic thio group, a sulfamoyl group, a sulfo group, alkyl- and aryl sulfinyl groups, alkyl- and aryl sulfonyl groups, alkyloxy- and aryloxycarbonyl groups, a carbamoyl group, aryl- and heterocyclic azo group, an imido group, a phosphino group, a phosphinyl group, a phosphinyloxy group, a phosphinylamino group, a phosphono group, a silyl group (a ditrimethylsiloxy methylbutoxy group), a hydrazino group, a ureido group, a boronic acid group ($—B(OH)_2$), a phosphate group ($—OPO(OH)_2$), a sulfate group ($—OSO_3H$), and other known substituents.

These substituents may further have the substituents described above.

Among these, as substituents that can be adopted, a halogen atom, an aryl group, an alkenyl group, an alkynyl group, a heterocyclic group, an alkoxy group, an alkylthio group, an acyloxy group, an aryloxy group, and an alkyloxycarbonyl group are preferable, a fluorine atom, an aryl group having 6 to 20 carbon atoms, an alkenyl group (preferably a 1-alkenyl group) having 2 to 12 carbon atoms, an alkynyl group having 2 to 12 carbon atoms, an alkoxy group having 1 to 11 carbon atoms, an acyloxy group, an alkylthio group having 1 to 12 carbon atoms, and an alkyloxycarbonyl group are more preferable, a halogen atom, an alkoxy group, an acyloxy group, and an alkyloxycarbonyl group are particularly preferable, and a halogen atom and an alkoxy group are most preferable.

In a case where each of $R^{11}$ and $R^{12}$ is an alkyl group substituted with a fluorine atom, some of the hydrogen atoms of the alkyl group may be substituted with a fluorine atom, or all of the hydrogen atoms may be substituted with a fluorine atom such that a perfluoroalkyl group is formed.

Here, each of $R^{11}$ and $R^{12}$ is preferably an unsubstituted linear or branched alkyl group.

In a case where each of $R^{11}$ and $R^{12}$ is a substituted linear alkyl group having 3 to 15 carbon atoms, the linear alkyl group is preferably a substituted linear alkyl group having 3 to 13 carbon atoms, more preferably a substituted linear alkyl group having 3 to 11 carbon atoms, particularly preferably a substituted linear alkyl group having 5 to 11 carbon atoms, and more particularly preferably a substituted linear alkyl group having 7 to 11 carbon atoms.

In a case where each of $R^{11}$ and $R^{12}$ is a substituted branched alkyl group having 3 to 18 carbon atoms, the branched alkyl group is preferably a substituted branched alkyl group having 3 to 15 carbon atoms, more preferably a substituted branched alkyl group having 3 to 13 carbon atoms, particularly preferably a substituted branched alkyl group having 3 to 11 carbon atoms, and more particularly preferably a substituted branched alkyl group having 7 to 11 carbon atoms.

In a case where each of $R^{11}$ and $R^{12}$ is a linear or branched alkyl group having a substituent, each of —$CH_2$— groups not being adjacent to each other in the linear alkyl group, —$CH_2$— groups not being adjacent to each other in the branched alkyl group, a trivalent tertiary carbon atom linking group, and a tetravalent quaternary carbon atom linking group may be independently substituted with other atom linking groups. In this case, example of other atom linking groups include —O—, —S—, —CO—, —COO—, —OCO—, —COS—, —SCO—, —NRCO—, —CONR— (R represents a hydrogen atom or an alkyl group having 1 to 6 carbon atoms), and the like.

Here, in $R^{11}$ and $R^{12}$, each of —$CH_2$— groups not being adjacent to each other in the linear alkyl group, —$CH_2$— groups not being adjacent to each other in the branched alkyl group, a trivalent tertiary carbon atom linking group, and a tetravalent quaternary carbon atom linking group is preferably not substituted with other atom linking groups.

In the present invention, each of $R^{11}$ and $R^{12}$ in the compound, which is represented by Formula (2) and satisfies the condition A, preferably independently has 3 to 30 carbon atoms in total and represents an unsubstituted linear alkyl group having an even number of carbon atoms within a range of 8 to 10 carbon atoms or an unsubstituted linear alkyl group having an odd number of carbon atoms within a range of 3 to 15 carbon atoms, and an aromatic portion in Formula (2) may be substituted with a halogen atom.

In the present invention, each of $R^{11}$ and $R^{12}$ in the compound, which is represented by Formula (2) and satisfies the condition A, preferably independently has 3 to 30 carbon atoms in total and represents a linear alkyl group having 3 to 15 carbon atoms substituted with a substituent through an ether structure or an ester bond.

Examples of the substituent substituted through an ether structure or an ester bond include the substituents that can be adopted for $R^{11}$ and $R^{12}$, and among these, an alkyl group is preferable, and a linear alkyl group is more preferable. The number of carbon atoms of the substituent substituted through an ether structure or an ester bond is preferably 1 to 10, more preferably 1 to 5, and particularly preferably 2 to 5.

(Condition B)

In the present invention, the compound represented by Formula (2) more preferably satisfies the following condition B;

condition B: in Formula (2), $R^{11}$ and $R^{12}$ each independently have 3 to 30 carbon atoms in total and represent an unsubstituted linear alkyl group having an even number of carbon atoms within a range of 2 to 4 carbon atoms.

(Condition C)

In the present invention, the compound represented by Formula (2) more preferably satisfies the following condition C;

condition C: in Formula (2), $R^{11}$ and $R^{12}$ each independently have 3 to 30 carbon atoms in total and represent a substituted alkyl group having 1 or 2 carbon atoms.

Among the compounds satisfying the condition C, a compound is preferable in which $R^{11}$ and $R^{12}$ each independently have 3 to 30 carbon atoms in total and represent an alkyl group having 1 or 2 carbon atoms substituted with a substituent through an ether structure or an ester bond.

Examples of the substituent substituted through an ether structure or an ester bond include the substituents that can be adopted for $R^{11}$ and $R^{12}$. Among these, an alkyl group is preferable, and a linear alkyl group is more preferable. The number of carbon atoms of the substituent substituted through an ether structure or an ester bond is preferably 1 to 10, more preferably 1 to 5, and particularly preferably 2 to 5.

(Condition D)

In the present invention, the compound represented by Formula (2) more preferably satisfies the following condition D;

condition D: in Formula (2), $R^{11}$ and $R^{12}$ each independently have 3 to 30 carbon atoms in total, and $R^{11}$ and $R^{12}$ have different structures.

Among the compounds satisfying the condition D, a compound is preferable in which $R^{11}$ and $R^{12}$ each independently have 3 to 30 carbon atoms in total, $R^{11}$ represents an unsubstituted linear alkyl group, and $R^{12}$ represents a substituted or unsubstituted linear or branched alkyl group different from $R^{11}$. Particularly, a compound is preferable in which $R^{11}$ and $R^{12}$ each independently have 3 to 30 carbon atoms in total and represent an unsubstituted linear alkyl group, and $R^{11}$ and $R^{12}$ have different structures.

The total number of carbon atoms that $R^{11}$ and $R^{12}$ each independently have is preferably 3 to 30, more preferably 7 to 30, particularly preferably 7 to 20, more particularly preferably 7 to 15, even more particularly preferably 7 to 11, and still more particularly preferably 9 to 11. If the total number of carbon atoms that $R^{11}$ and $R^{12}$ each independently have is equal to or greater than the lower limit of the above range, carrier mobility is improved. If the total number of carbon atoms of $R^{11}$ and $R^{12}$ is equal to or less than the upper limit of the above range, solubility in an organic solvent is improved.

Specific examples of the compound represented by Formula (2) will be shown below, but the compound represented by Formula (2) that can be used in the present invention is not limited to the following specific examples. Herein, $R^{11}$ and $R^{12}$ in the following Tables 1 and 2 represent $R^{11}$ and $R^{12}$ in Formula (2).

TABLE 1

| Compound | $R^{11}$ | $R^{12}$ |
| --- | --- | --- |
| Compound 1 | n-$C_{10}H_{21}$ | n-$C_{10}H_{21}$ |
| Compound 2 | $C_2H_5$ | $C_2H_5$ |
| Compound 3 | n-$C_3H_7$ | n-$C_3H_7$ |
| Compound 4 | n-$C_4H_9$ | n-$C_4H_9$ |
| Compound 5 | n-$C_5H_{11}$ | n-$C_5H_{11}$ |
| Compound 6 | n-$C_6H_{13}$ | n-$C_6H_{13}$ |
| Compound 7 | n-$C_7H_{15}$ | n-$C_7H_{15}$ |
| Compound 8 | n-$C_8H_{17}$ | n-$C_8H_{17}$ |
| Compound 9 | n-$C_9H_{19}$ | n-$C_9H_{19}$ |
| Compound 10 | n-$C_{12}H_{25}$ | n-$C_{12}H_{25}$ |
| Compound 11 | (branched alkyl structure) | (branched alkyl structure) |
| Compound 12 | (cyclohexylmethyl structure) | (cyclohexylmethyl structure) |
| Compound 13 | (alkenyl structure) | (alkenyl structure) |
| Compound 14 | $(CH_2)_4F$ | $(CH_2)_4F$ |

TABLE 1-continued

| Compound | $R^{11}$ | $R^{12}$ |
|---|---|---|
| Compound 15 | (CH$_2$)$_3$Ph | (CH$_2$)$_3$Ph |
| Compound 16 | 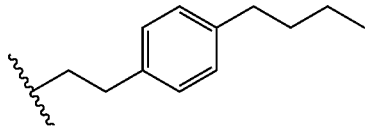 [SMILES: *CCc1ccc(CCCC)cc1] | 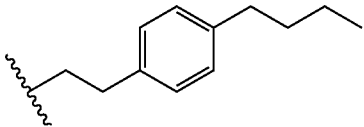 [SMILES: *CCc1ccc(CCCC)cc1] |
| Compound 17 | 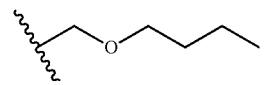 [SMILES: *COCCCC] | 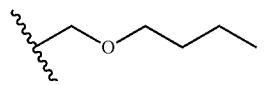 [SMILES: *COCCCC] |
| Compound 18 | 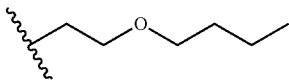 [SMILES: *CCOCCCC] | 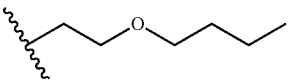 [SMILES: *CCOCCCC] |
| Compound 19 | 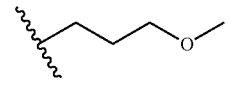 [SMILES: *CCCOC] | 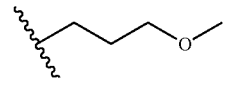 [SMILES: *CCCOC] |
| Compound 20 | 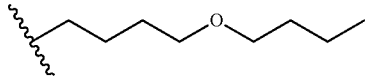 [SMILES: *CCCCOCCCC] | 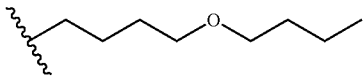 [SMILES: *CCCCOCCCC] |
| Compound 21 | 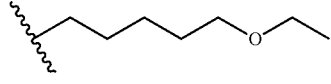 [SMILES: *CCCCCOCC] | 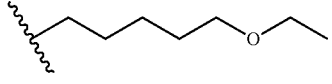 [SMILES: *CCCCCOCC] |
| Compound 22 | 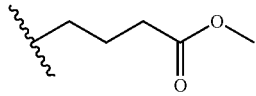 [SMILES: *CCCC(=O)OC] | 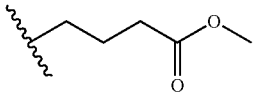 [SMILES: *CCCC(=O)OC] |
| Compound 23 | 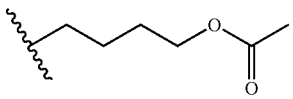 [SMILES: *CCCCOC(C)=O] | 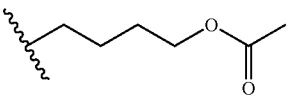 [SMILES: *CCCCOC(C)=O] |
| Compound 24 | 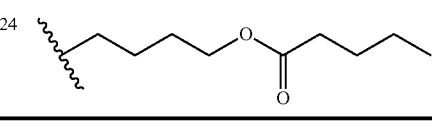 | 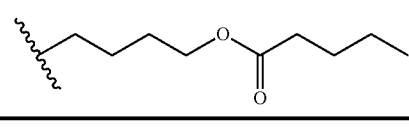 |

TABLE 2

| Compound | $R^{11}$ | $R^{12}$ |
|---|---|---|
| Compound 25 | C$_2$H$_5$ | n-C$_4$H$_9$ |
| Compound 26 | C$_2$H$_5$ | n-C$_6$H$_{13}$ |
| Compound 27 | n-C$_3$H$_7$ | n-C$_6$H$_{13}$ |
| Compound 28 | n-C$_3$H$_7$ | n-C$_4$H$_9$ |
| Compound 29 | n-C$_4$H$_9$ | n-C$_5$H$_{11}$ |
| Compound 30 | n-C$_4$H$_9$ | n-C$_6$H$_{13}$ |
| Compound 31 | n-C$_4$H$_9$ | n-C$_8$H$_{17}$ |
| Compound 32 | n-C$_4$H$_9$ | n-C$_{12}$H$_{25}$ |
| Compound 33 | n-C$_5$H$_{11}$ | n-C$_6$H$_{13}$ |
| Compound 34 | n-C$_8$H$_{17}$ | 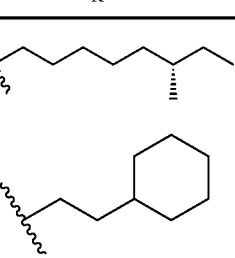 |
| Compound 35 | n-C$_8$H$_{17}$ | 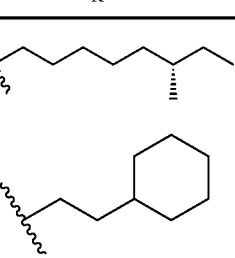 |
| Compound 36 | n-C$_{12}$H$_{25}$ | (CH$_2$)$_4$F |
| Compound 37 | n-C$_8$H$_{17}$ | (CH$_2$)$_3$Ph |
| Compound 38 | n-C$_4$H$_9$ | 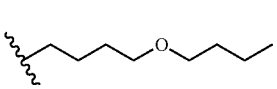 [SMILES: *CCCCOCCCC] |

TABLE 2-continued
| Compound | R[11] | R[12] |
|---|---|---|
| Compound 39 | n-C$_{12}$H$_{25}$ | 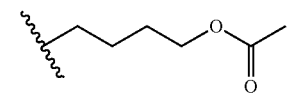 [SMILES: *CCCCOC(C)=O] |
| Compound 40 | | |
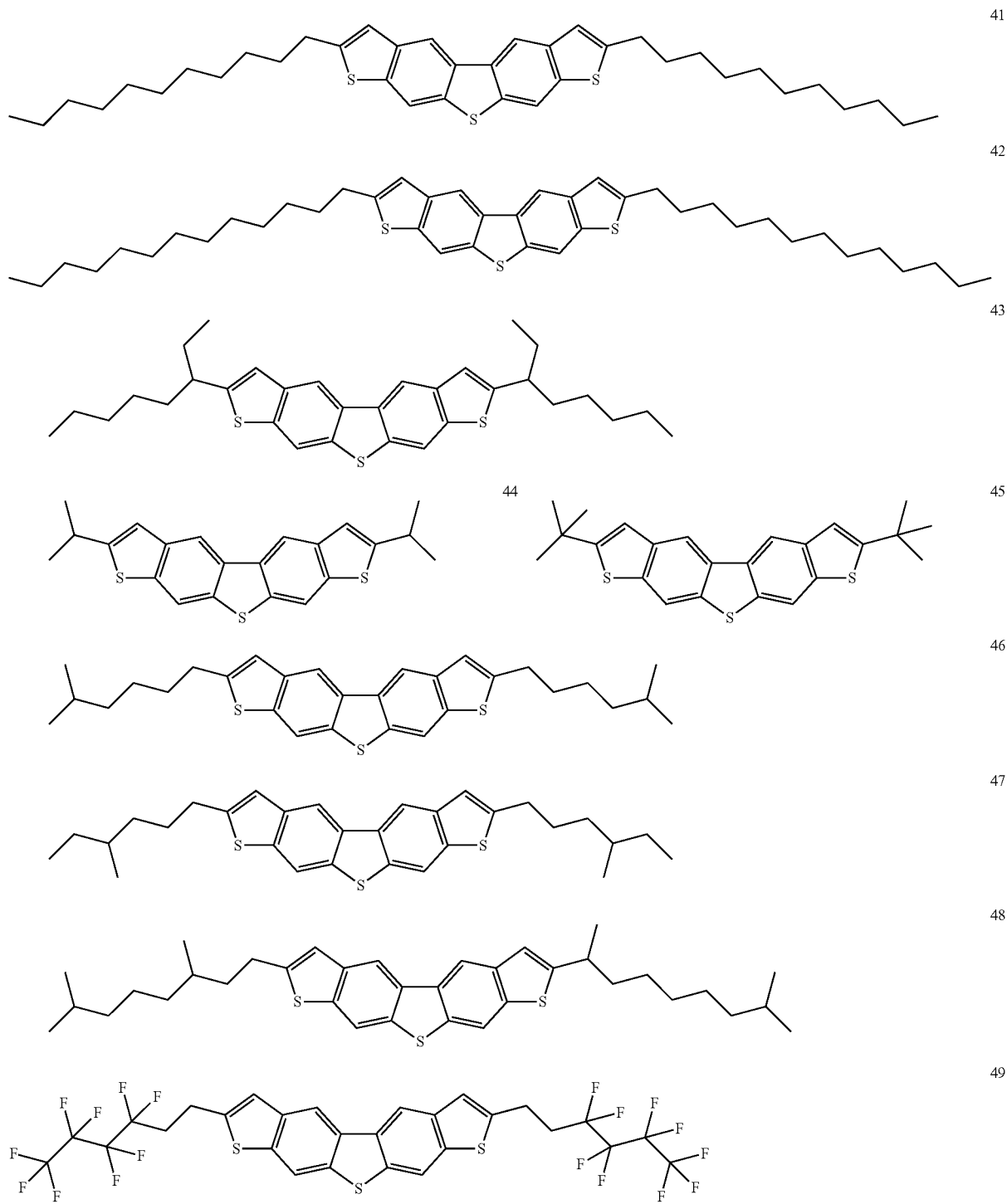

-continued

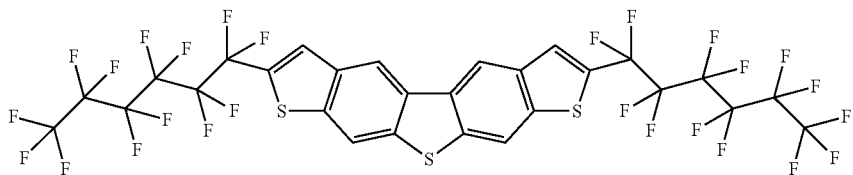
50

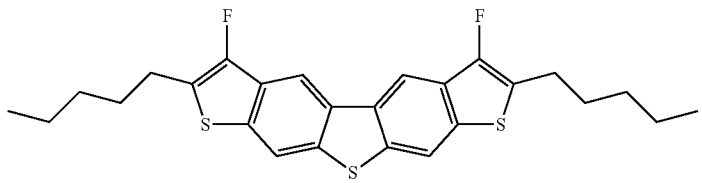
51

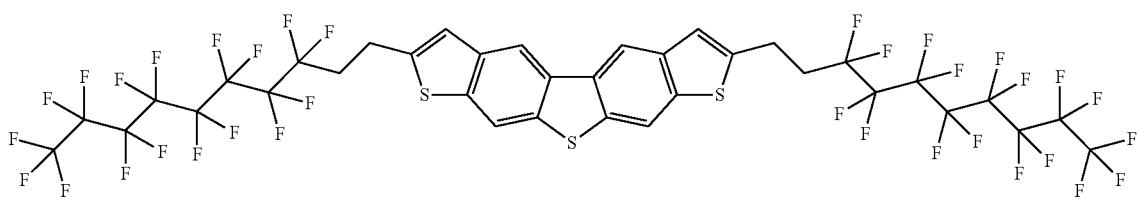
52

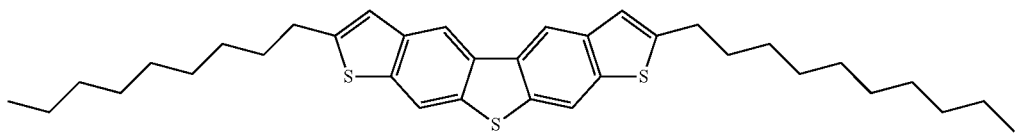
53

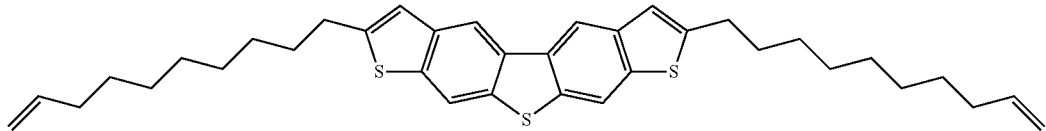
54

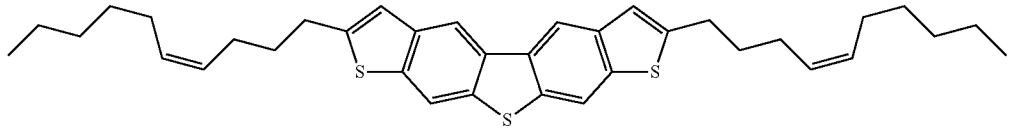
55

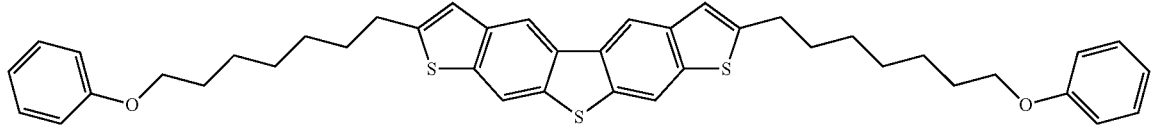
56

The molecular weight of the compound represented by Formula (2) is preferably equal to or less than 3,000, more preferably equal to or less than 2,000, even more preferably equal to or less than 1,000, and particularly preferably equal to or less than 850. It is preferable that the molecular weight is equal to or less than the above upper limit, because then the solubility of the compound in a solvent can be improved.

From the viewpoint of film quality stability of the film, the molecular weight is preferably equal to or greater than 250, more preferably equal to or greater than 300, and even more preferably equal to or greater than 350.

The compound represented by Formula (2) can be synthesized with reference to the method described in Tetrahedron 66 (2010) 8778-8784 or the method described in examples which will be described later.

For synthesizing the compound represented by Formula (2), any of reaction conditions may be used. As a reaction solvent, any of solvents may be used. Furthermore, in order to accelerate a ring-forming reaction, an acid or a base is preferably used, and an acid is particularly preferably used. Although optimal reaction conditions vary with the structure of the intended compound, they can be set with reference to the specific reaction conditions described in the aforementioned documents or the method described in examples which will be described later.

A synthetic intermediate having various substituents can be synthesized using known reactions in combination. Furthermore, various substituents may be introduced into the intermediate at any stage. After the intermediate is synthesized, it is preferable to purify the intermediate by column chromatography, recrystallization, or the like and then further purify it by sublimation. By the sublimation purifica- <Solvent>

In a case where a film is formed on a substrate by using a solution process, by using a coating solution, which is obtained by dissolving or dispersing a material for forming a layer in an appropriate organic solvent (for example, a hydrocarbon-based solvent such as hexane, octane, decane, toluene, xylene, mesitylene, ethylbenzene, amylbenzene, decalin, 1-methylnaphthalene, 1-ethylnaphthalene, 1,6-dimethylnaphthalene, or tetralin, a ketone-based solvent such as acetone, methyl ethyl ketone, methyl isobutyl ketone, cyclohexanone, acetophenone, propiophenone, butyrophenone, α-tetralone, or β-tetralone, a halogenated hydrocarbon-based solvent such as dichloroethane, chloroform, tetrachloromethane, dichloroethane, trichloroethane, tetrachloroethane, chlorobenzene, 1,2-dichlorobenzene, 1,2,4-trichlorobenzene, chlorotoluene, or 1-fluoronaphthalene, a heterocyclic solvent such as pyridine, picoline, quinoline, thiophene, 3-butylthiophene, or thieno[2,3-b]thiophene, a halogenated heterocyclic solvent such as 2-chlorothiophene, 3-chlorothiophene, 2,5-dichlorothiophene, 3,4-dichlorothiophene, 2-bromothiophene, 3-bromothiophene, 2,3-dibromothiophene, 2,4-dibromothiophene, 2,5-dibromothiophene, 3,4-dibromothiophene, or 3,4-dichloro-1,2,5-thiadiazole, an ester-based solvent such as ethyl acetate, butyl acetate, amyl acetate, 2-ethylhexyl acetate, γ-butyrolactone, or phenyl acetate, an alcohol-based solvent such as methanol, propanol, butanol, pentanol, hexanol, cyclohexanol, methyl cellosolve, ethyl cellosolve, or ethylene glycol, an ether-based solvent such as dibutyl ether, tetrahydrofuran, dioxane, dimethoxyethane, anisole, ethoxybenzene, propoxybenzene, isopropoxybenzene, butoxybenzene, 2-methylanisole, 3-methylanisole, 4-methylanisole, 4-ethylanisole, dimethylanisole (any of 2,3-, 2,4-, 2,5-, 2,6-, 3,4-, 3,5-, and 3,6-dimethylanisoles), or 1,4-benzodioxane, 2,3-dihydrobenzofuran, phthalan, chroman, or isochroman, an amide/imide-based solvent such as N,N-dimethylformamide, N,N-dimethylacetamide, 1-methyl-2-pyrrolidone, 1-methyl-2-imidazolidinone, or 1,3-dimethyl-2-imidazolidinone, a sulfoxide-based solvent such as dimethylsulfoxide, a phosphoric acid ester-based solvent such as trimethyl phosphate, a nitrile-based solvent such as acetonitrile or benzonitrile, a nitro-based solvent such as nitromethane or nitrobenzene) and/or water, a film can be formed by various coating methods. One kind of solvent may be used singly, or plural kinds thereof may be used in combination. Among these, a hydrocarbon-based solvent, a ketone-based solvent, a halogenated hydrocarbon-based solvent, a heterocyclic solvent, a halogenated heterocyclic solvent, or an ether-based solvent is preferable, toluene, xylene, mesitylene, amylbenzene, tetralin, acetophenone, propiophenone, butyrophenone, α-tetralone, dichlorobenzene, anisole, ethoxybenzene, propoxybenzene, isopropoxybenzene, butoxybenzene, 2-methylanisole, 3-methylanisole, 4-methylanisole, 2,3-dihydrobenzofuran, phthalan, chroman, isochroman 1-fluoronaphthalene, 3-chlorothiophene, and 2,5-dibromothiophene are more preferable, and toluene, xylene, tetralin, acetophenone, propiophenone, butyrophenone, α-tetralone, anisole, ethoxybenzene, propoxybenzene, butoxybenzene, 2-methylanisole, 3-methylanisole, 4-methylanisole, 2,3-dihydrobenzofuran, phthalan, chroman, isochroman, 1-fluoronaphthalene, 3-chlorothiophene, and 2,5-dibromothiophene are particularly preferable.

In the first aspect of the coating solution for a non-light-emitting organic semiconductor device of the present invention, among these solvents, a solvent having a boiling point of equal to or higher than 100° C. is used. In the first aspect of the coating solution for a non-light-emitting organic semiconductor device of the present invention, the coating solution contains a solvent having a boiling point of equal to or higher than 100° C., and this results in an advantage that excellent film quality and crystals with a large area can be obtained. The coating solution of the first aspect is suitably used in a method for manufacturing an organic semiconductor film of the present invention Furthermore, in the second aspect of the coating solution for a non-light-emitting organic semiconductor device of the present invention, it is preferable to use a solvent having a boiling point of equal to or higher than 100° C. from the same standpoint as described above.

From the viewpoint described above, the boiling point of the solvent having a boiling point of equal to or higher than 100° C. is preferably equal to or higher than 150° C., more preferably equal to or higher than 175° C., and particularly preferably equal to or higher than 200° C.

In addition, from the viewpoint of environmental load and toxicity to human beings, the solvent having a boiling point of equal to or higher than 100° C. is preferably a non-halogen-based solvent.

The concentration of the compound represented by Formula (2) in the coating solution is preferably 0.005% to 5% by mass, more preferably 0.01% to 3% by mass, and particularly preferably 0.1% to 2% by mass. If the concentration is within the above range, a film with arbitrary thickness is easily formed. Furthermore, it is particularly preferable that the concentration of the compound represented by Formula (2) in the coating solution for a non-light-emitting organic semiconductor device is equal to or greater than 0.4% by mass, because then a coating film composed of large-sized crystals is easily formed. Although Tetrahedron 66 (2010) 8778-8784 describes a low-concentration solution for measuring oxidation-reduction potential or emission/absorption, from the viewpoint described above, it is preferable that the concentration of the coating solution for a non-light-emitting organic semiconductor device is high.

For the coating solution for a non-light-emitting organic semiconductor device of the present invention, an aspect is also preferable in which the coating solution contains the compound represented by Formula (2) but does not contain a polymer binder.

Furthermore, the coating solution for a non-light-emitting organic semiconductor device of the present invention may contain the compound represented by Formula (2) and a polymer binder. In this case, by using a coating solution obtained by dissolving or dispersing a material, which will be formed into a layer, and a polymer binder in an appropriate solvent described above, a film can be formed by various coating methods. The polymer binder can be selected from those which will be described later.

From the viewpoint of the film quality uniformity of the coating film to be formed, the coating solution for a non-light-emitting organic semiconductor device preferably contains a polymer.

The coating solution for a non-light-emitting organic semiconductor device may contain only one kind of compound represented by Formula (2) or contain two or more kinds thereof. From the viewpoint of the storage stability (inhibition of crystal precipitation during storage) of the coating solution, the coating solution preferably contains two or more kinds of compound represented by Formula (2).

From the viewpoint of the suitability for various printing methods, the coating solution for a non-light-emitting organic semiconductor device preferably has a viscosity of equal to or greater than 10 mPa·s.

The coating solution for a non-light-emitting organic semiconductor device may contain additives other than a polymer binder, such as a surfactant, an antioxidant, a crystallization control agent, and a crystal orientation control agent.

Examples of the surfactant are not particularly limited and include nonionic surfactants such as polyoxyethylene alkyl ethers, polyoxyethylene alkyl allyl ethers, polyoxyethylene-polyoxypropylene block copolymers, sorbitan fatty acid esters, and a polyoxyethylene sorbitan fatty acid ester; fluorine-based surfactants such as MEGAFACE F171 and F176 (manufactured by DIC Corporation), FLUORAD FC430 (manufactured by Sumitomo 3M Ltd.), SURFYNOL E1004 (manufactured by ASAHI GLASS CO., LTD.), and PF656 and PF6320 manufactured by OMNOVA Solutions Inc.; and organosiloxane polymers such as polysiloxane polymers KP-341 (manufactured by Shin-Etsu Chemical Co., Ltd.), KF-410 (manufactured by Shin-Etsu Chemical Co., Ltd.), KF-412 (manufactured by Shin-Etsu Chemical Co., Ltd.), KF-96-100cs (manufactured by Shin-Etsu Chemical Co., Ltd.), BYK-322 (manufactured by BYK Additives & Instruments), and BYK-323 (manufactured by BYK Additives & Instruments).

The content of the surfactant in the coating solution is preferably about 0.001% to 1% by mass.

Examples of the antioxidant include a phenol-based antioxidant, a phosphorus-based antioxidant, a sulfur-based antioxidant, and the like.

Specific examples of the phenol-based antioxidant include 2,6-di-t-butyl-4-methylphenol, n-octadecyl-3-(3',5'-di-t-butyl-4'-hydroxyphenyl)propionate, tetrakis[methylene-3-(3,5-di-t-butyl-4-hydroxyphenyl)propionate]methane, tris(3,5-di-t-butyl-4-hydroxybenzyl)isocyanurate, 4,4'-butylidenebis-(3-methyl-6-t-butylphenol), triethylene glycol bis[3-(3-t-butyl-4-hydroxy-5-methylphenyl)propionate], and 3,9-bis {2-[3-(3-t-butyl-4-hydroxy-5-methylphenyl) propionyloxy]-1,1-dimethylethyl}-2,4,8,10-tetraoxaspiro[5,5]undecane.

Examples of commercially available products of the phenol-based antioxidant include IRGANOX 1010, IRGANOX 1035, IRGANOX 1076, IRGANOX 1135, IRGANOX 245, IRGANOX 259, IRGANOX 295, and IRGANOX 3114 (all manufactured by BASF SE), ADEKA STAB AO-20, ADEKA STAB AO-30, ADEKA STAB AO-40, ADEKA STAB AO-50, ADEKA STAB AO-60, ADEKA STAB AO-70, ADEKA STAB AO-80, ADEKA STAB AO-90, and ADEKA STAB AO-330 (all manufactured by ADEKA Corporation), SUMILIZER BHT, SUMILIZER BP-101, SUMILIZER GA-80, SUMILIZER MDP-S, SUMILIZER BBM-S, SUMILIZER GM, SUMILIZER GS(F), and SUMILIZER GP (all manufactured by Sumitomo Chemical Co., Ltd.), HOSTANOX 010, HOSTANOX 016, HOSTANOX 014, and HOSTANOX 03 (all manufactured by CLARIANT), ANTAGE BHT, ANTAGE W-300, ANTAGE W-400, and ANTAGE W-500 (all manufactured by Kawaguchi Chemical Industry Co., LTD.), SEENOX 224M and SEENOX 326 M (all manufactured by SHIPRO KASEI KAISHA, LTD.), YOSHINOX BHT, YOSHINOX BB, TOMINOX TT, and TOMINOX 917 (all manufactured by YOSHITOMI PHARMACEUTICAL INDUSTRIES, LTD.), TTHP (manufactured by TORAY INDUSTRIES, INC.), and the like.

Specific examples of the phosphorus-based antioxidant include trisnonylphenyl phosphite, tris(2,4-di-t-butylphenyl) phosphite, distearyl pentaerythritol diphosphite, bis(2,4-di-t-butylphenyl)pentaerythritol phosphite, bis(2,6-di-t-butyl-4-methylphenyl)pentaerythritol phosphite, 2,2-methylenebis(4,6-di-t-butylphenyl)octylphosphite, tetrakis (2,4-di-t-butylphenyl)-4,4-biphenylene-di-phosphonite, and the like. Examples of commercially available products of the phosphorus-based antioxidant include ADEKA STAB 1178 (manufactured by ADEKA Corporation), SUMILIZER TNP (manufactured by Sumitomo Chemical Co., Ltd.), JP-135 (manufactured by JOHOKU CHEMICAL CO., LTD), ADEKA STAB 2112 (manufactured by ADEKA Corporation), JPP-2000 (manufactured by JOHOKU CHEMICAL CO., LTD), WESTON 618 (manufactured by General Electric), ADEKA STAB PEP-24G (manufactured by ADEKA Corporation), ADEKA STAB PEP-36 (manufactured by ADEKA Corporation), ADEKA STAB HP-10 (manufactured by ADEKA Corporation), SANDSTAB P-EPQ (manufactured by Sandoz), PHOSPHITE 168 (manufactured by Ciba Specialty Chemicals, Inc.), and the like.

Specific examples of the sulfur-based antioxidant include dilauryl-3,3'-thiodipropionate, dimyristyl-3,3'-thiodipropionate, distearyl-3,3'-thiodipropionate, pentaerythritol tetrakis(3-laurylthiopropionate), and the like. Examples of commercially available products of the sulfur-based antioxidant include SUMILIZER TPL (manufactured by Sumitomo Chemical Co., Ltd.), YOSHINOX DLTP (manufactured by YOSHITOMI PHARMACEUTICAL INDUSTRIES, LTD.), ANTIOX L (manufactured by NOF CORPORATION), SUMILIZER TPM (manufactured by Sumitomo Chemical Co., Ltd.), YOSHINOX DMTP (manufactured by YOSHITOMI PHARMACEUTICAL INDUSTRIES, LTD.), ANTIOX M (manufactured by NOF CORPORATION), SUMILIZER TPS (manufactured by Sumitomo Chemical Co., Ltd.), YOSHINOX DSTP (manufactured by YOSHITOMI PHARMACEUTICAL INDUSTRIES, LTD.), ANTIOX S (manufactured by NOF CORPORATION), ADEKA STAB AO-412S (manufactured by ADEKA Corporation), SEENOX 412S (manufactured by SHIPRO KASEI KAISHA, LTD.), SUMILIZER TDP (manufactured by Sumitomo Chemical Co., Ltd.), and the like.

The content of the antioxidant in the coating solution is preferably about 0.01% to 5% by mass.

<Structure of Organic Transistor>

The first aspect of the organic transistor of the present invention contains the compound represented by Formula (2) in a semiconductor active layer.

The second aspect of the organic transistor of the present invention contains the compound of the present invention in a semiconductor active layer.

That is, the organic transistor of the present invention has a semiconductor active layer containing the compound represented by Formula (2).

The organic transistor of the present invention may further have layers other than the semiconductor active layer.

The organic transistor of the present invention is preferably used as an organic field effect transistor (FET), and is more preferably used as an insulated gate-type FET in which the gate is insulated from channels.

Hereinafter, preferred structural aspects of the organic transistor of the present invention will be specifically described by using drawings, but the present invention is not limited to the aspects.

(Lamination Structure)

The lamination structure of an organic field effect transistor is not particularly limited, and various known structures can be adopted.

For example, the organic transistor of the present invention can adopt a structure (bottom gate/top contact type) in which an electrode, an insulator layer, a semiconductor active layer (organic semiconductor layer), and two electrodes are arranged in this order on the upper surface of a substrate which is a lower most layer. In this structure, the electrode on the upper surface of the substrate as the lower most layer is provided in a portion of the substrate, and the insulator layer is so disposed that it comes into contact with the substrate in a portion other than the electrode. The two electrodes provided on the upper surface of the semiconductor active layer are arranged in a state of being separated from each other.

Figure 1:
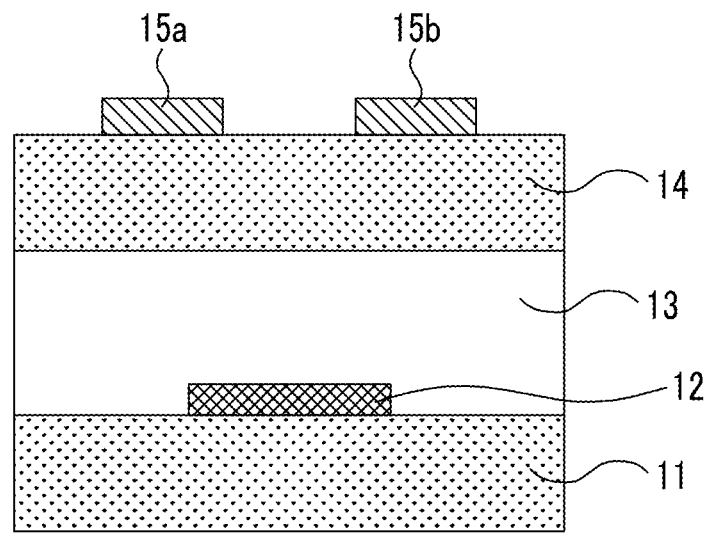
FIG. 1 is a schematic view showing a section of an exemplary structure of an organic transistor manufactured as a substrate for measuring FET characteristics in examples of the present invention.

FIG. 1 shows the constitution of a bottom gate/top contact-type element. FIG. 1 is a schematic view showing a section of an exemplary structure of the organic transistor of the present invention. In the organic transistor shown in FIG. 1, a substrate 11 is disposed as a lower most layer, an electrode 12 is provided in a portion of the upper surface thereof, and an insulator layer 13 is provided such that it covers the electrode 12 and contacts the substrate 11 in a portion other than the electrode 12. On the upper surface of the insulator layer 13, a semiconductor active layer 14 is provided, and in a portion of the upper surface thereof, two electrodes 15a and 15b are arranged in a state of being separated from each other.

In the organic transistor shown in FIG. 1, the electrode 12 is a gate, and the electrode 15a and the electrode 15b are a drain and a source respectively. The organic transistor shown in FIG. 1 is an insulated gate-type FET in which a channel as a path of electric currents between the drain and the source is insulated from the gate.

As an example of the structure of the organic transistor of the present invention, a bottom gate/bottom contact-type element can be exemplified.

Figure 2:
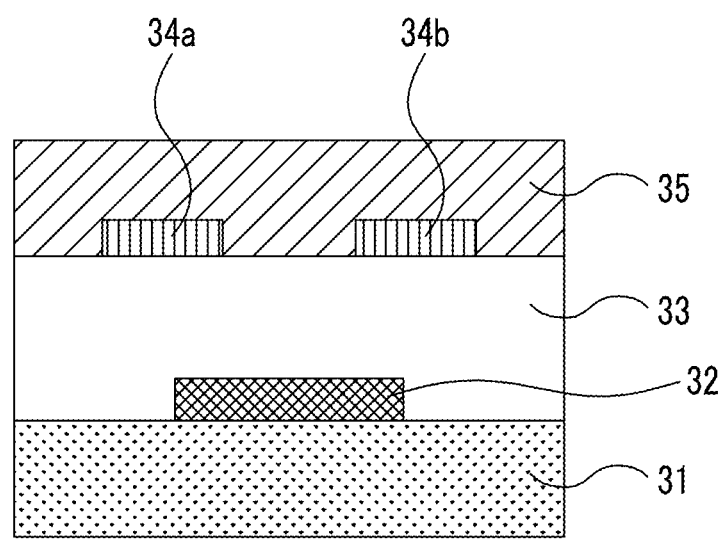
FIG. 2 is a schematic view showing a section of the structure of the organic transistor manufactured as a substrate for measuring FET characteristics in examples of the present invention.

FIG. 2 shows the constitution of the bottom gate/bottom contact-type element. FIG. 2 is a schematic view showing a section of the structure of an organic transistor manufactured as a substrate for measuring FET characteristics in examples of the present invention. In the organic transistor shown in FIG. 2, a substrate 31 is disposed as a lower most layer, an electrode 32 is provided in a portion of the upper surface thereof, and an insulator layer 33 is provided such that it covers the electrode 32 and comes into contact with the substrate 31 in a portion other than the electrode 32. Furthermore, a semiconductor active layer 35 is provided on the upper surface of the insulator layer 33, and electrodes 34a and 34b are in a lower portion of the semiconductor active layer 35.

In the organic transistor shown in FIG. 2, the electrode 32 is a gate, and the electrode 34a and the electrode 34b are a drain and a source respectively. The organic transistor shown in FIG. 2 is an insulated gate-type FET in which a channel as a path of electric currents between the drain and the source is insulated from the gate.

As the structure of the organic transistor of the present invention, a top gate/top contact-type element in which an insulator and a gate electrode are in the upper portion of a semiconductor active layer or a top gate/bottom contact-type element can also be preferably used.

(Thickness)

In a case where the organic transistor of the present invention needs to be a thinner transistor, the total thickness of the transistor is preferably, for example, 0.1 µm to 0.5 µm.

(Sealing)

In order to improve the preservation stability of the organic transistor element by blocking the organic transistor element from the atmosphere or moisture, the entirety of the organic transistor element may be sealed with a metal sealing can, glass, an inorganic material such as silicon nitride, a polymer material such as perylene, a low-molecular weight material, or the like.

Hereinafter, preferred aspects of the respective layers of the organic transistor of the present invention will be described, but the present invention is not limited to the aspects.

<Substrate>
(Material)

The organic transistor of the present invention preferably includes a substrate.

The material of the substrate is not particularly limited, and known materials can be used. Examples of the material include a polyester film such as polyethylene naphthalate (PEN) or polyethylene terephthalate (PET), a cycloolefin polymer film, a polycarbonate film, a triacetylcellulose (TAC) film, a polyimide film, a material obtained by bonding these polymer films to extremely thin glass, ceramics, silicon, quartz, glass, and the like. Among these, silicon is preferable.

<Electrode>
(Material)

The organic transistor of the present invention preferably includes an electrode.

As the material constituting the electrode, known conductive materials such as a metal material like Cr, Al, Ta, Mo, Nb, Cu, Ag, Au, Pt, Pd, In, Ni, or Nd, an alloy material of these, a carbon material, and a conductive polymer can be used without particular limitation.

(Thickness)

The thickness of the electrode is not particularly limited, but is preferably 10 nm to 50 nm.

A gate width (or a channel width) W and a gate length (or a channel length) L are not particularly limited. However, a ratio of W/L is preferably equal to or greater than 10, and more preferably equal to or greater than 20.

<Acceptor>
(Material)

The organic transistor of the present invention may include an acceptor for accelerating injection of carriers. Preferred examples of the material include known 2,3,5,6-tetrafluoro-7,7,8,8-tetracyanoquinodimethane (F4-TCNQ) and the like.

(Thickness)

The thickness of the acceptor is not particularly limited and is preferably equal to or less than 5 nm.

<Insulating Layer>
(Material)

The material constituting the insulating layer is not particularly limited as long as a necessary insulating effect is obtained. Examples of the material include silicon dioxide, silicon nitride, a fluorine polymer-based insulating material such as polytetrafluoroethylene (PTFE) or CYTOP, a polyester insulating material, a polycarbonate insulating material, an acryl polymer-based insulating material, an epoxy resin-based insulating material, a polyimide insulating material, a polyvinyl phenol resin-based insulating material, a poly p-xylylene resin-based insulating material, and the like.

A surface treatment may be performed on the upper surface of the insulating layer. For example, it is possible to preferably use an insulating layer in which the silicon dioxide surface thereof is subjected to the surface treatment by being coated with hexamethyldisilazane (HMDS), octadecyltrichlorosilane (OTS), or β-phenethyltrimethoxysilane.

(Thickness)

The thickness of the insulating layer is not particularly limited. However, in a case where the film needs to be thinned, the thickness of the insulating layer is preferably 10 nm to 500 nm, more preferably 20 nm to 200 nm, and particularly preferably 50 nm to 200 nm.

<Semiconductor Active Layer>

(Material)

The organic transistor of the present invention contains the compound represented by Formula (2) in the semiconductor active layer.

The semiconductor active layer may be a layer further containing a polymer binder (referred to as a polymer or a binder as well) in addition to the compound represented by Formula (2). Furthermore, the semiconductor active layer may contain a residual solvent used at the time of forming a film.

The content of the polymer binder in the semiconductor active layer is not particularly limited. The content of the polymer binder used is preferably within a range of 0% to 95% by mass, more preferably within a range of 10% to 90% by mass, even more preferably within a range of 20% to 80% by mass, and particularly preferably within a range of 30% to 70% by mass.

(Thickness)

The thickness of the semiconductor active layer is not particularly limited. In a case where the film needs to be thinned, the thickness of the semiconductor active layer is preferably 10 nm to 400 nm, more preferably 10 nm to 200 nm, and particularly preferably 10 nm to 100 nm.

[Method for Manufacturing Organic Transistor]

A method for manufacturing an organic transistor of the present invention includes a step of preparing a semiconductor active layer by coating a substrate with a coating solution for a non-light-emitting organic semiconductor device of the present invention and drying the coating solution.

The method for manufacturing an organic transistor of the present invention may or may not include a method for manufacturing an organic semiconductor film of the present invention that will be described later.

First, general methods in the method for manufacturing an organic transistor of the present invention will be described.

(Film Forming Method)

In the method for manufacturing an organic transistor of the present invention, the compound of the present invention or the compound represented by Formula (2) may be formed into a film on a substrate by any method.

At the time of forming the film, the substrate may be heated or cooled. By varying the temperature of the substrate, it is possible to control the film quality or the packing of molecules in the film. The temperature of the substrate is not particularly limited. The temperature is preferably between 0° C. to 200° C., more preferably between 15° C. to 120° C., and particularly preferably between 20° C. to 100° C.

The compound of the present invention or the compound represented by Formula (2) can be formed into a film on a substrate by a vacuum process or a solution process, and both of the processes are preferable.

Specific examples of the film forming method by a vacuum process include a physical vapor deposition method such as a vacuum vapor deposition method, a sputtering method, an ion plating method, or a molecular beam epitaxy (MBE) method and a chemical vapor deposition (CVD) method such as plasma polymerization, and it is particularly preferable to use a vacuum vapor deposition method.

Herein, the film forming method by a solution process refers to a method of dissolving an organic compound in a solvent which can dissolve the compound and forming a film by using the solution. Specifically, it is possible to use general methods like a coating method such as a casting method, a dip coating method, a die coater method, a roll coater method, a bar coater method, or a spin coating method, various printing methods such as an ink jet method, a screen printing method, a gravure printing method, a flexographic printing method, an offset printing method, or a micro-contact printing method, and a Langmuir-Blodgett (LB) method. It is particularly preferable to use a casting method, a spin coating method, an ink jet method, a gravure printing method, a flexographic printing method, an offset printing method, or a micro-contact printing method.

The organic semiconductor film for a non-light-emitting organic semiconductor device of the present invention is preferably prepared by a solution coating method. In a case where the organic semiconductor film for a non-light-emitting organic semiconductor device of the present invention contains a polymer binder, it is preferable to prepare a coating solution by dissolving or dispersing a material, which will be formed into a layer, and a polymer binder in an appropriate solvent and to form the organic semiconductor film by various coating methods.

Next, as a more preferred aspect in the method for manufacturing an organic transistor of the present invention, a method including the method for manufacturing an organic semiconductor film of the present invention will be described.

[Method for Manufacturing Organic Semiconductor Film]

In a first aspect of the method for manufacturing an organic semiconductor film of the present invention, in a state where a distance between a substrate A and a member B not being fixed to the substrate A is kept constant or in a state where the substrate A and the member B are caused to remain in contact with each other, a coating solution containing a compound represented by the following Formula (2) and a solvent having a boiling point of equal to or higher than 100° C. is dropped onto a portion within the surface of the substrate A such that the coating solution contacts both of the substrate A and the member B, and the dropped coating solution is slowly dried, such that crystals of the compound represented by Formula (2) are precipitated and a semiconductor active layer is formed; here, as long as the distance between the substrate A and the member B is kept constant or as long as the substrate A and the member B are caused to remain in contact with each other, the positional relationship between the substrate A and the member B may be maintained or changed when the coating solution is dropped or dried;

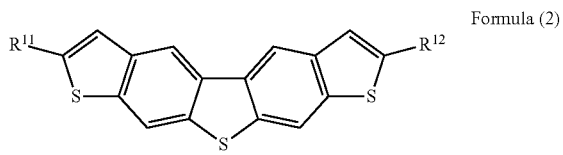

Formula (2)

in Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with a halogen atom.

In a second aspect of the method for manufacturing an organic semiconductor film of the present invention, in a state where a distance between a substrate A and a member B not being fixed to the substrate A is kept constant or in a state where the substrate A and the member B are caused to remain in contact with each other, a coating solution prepared by dissolving the compound of the present invention in a solvent is dropped onto a portion within the surface of the substrate A such that the coating solution contacts both of the substrate A and the member B, and the dropped coating solution is slowly dried, such that crystals of the compound of the present invention are precipitated and a semiconductor active layer is formed; here, as long as the distance between the substrate A and the member B is kept constant or as long as the substrate A and the member B are caused to remain in contact with each other, the positional relationship between the substrate A and the member B may be maintained or changed when the coating solution is dropped or dried.

Hereinafter, the first and second aspects of the method for manufacturing an organic semiconductor film of the present invention will be comprehensively described.

The preferred aspects of the method for manufacturing an organic semiconductor film of the present invention will be described based on drawings.

Figure 3A:
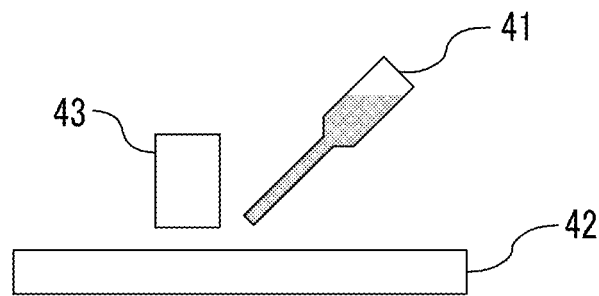
FIGS. 3A to 3C are schematic views showing an example of a method for manufacturing an organic semiconductor film of the present invention. Specifically.
Figure 3B:
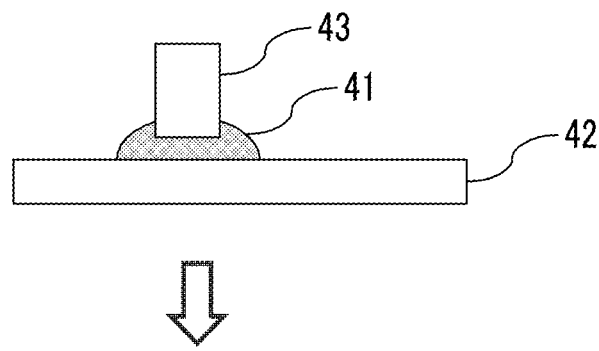
Figure 3C:
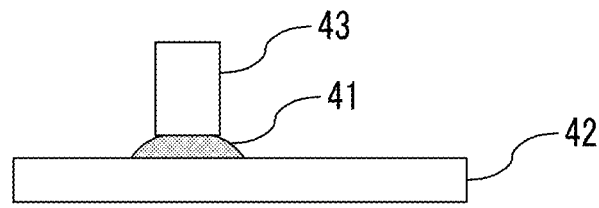

FIGS. 3A to 3C are schematic views showing an example of the method for manufacturing an organic semiconductor film of the present invention.

FIG. 3A shows a state where the coating solution (reference 41) has not yet been dropped onto the substrate A (reference 42). In this state, the distance between the substrate A (reference 42) and the member B (reference 43) not being fixed to the substrate A (reference 42) is kept constant.

FIG. 3B shows a state where the coating solution (reference 41) is then dropped onto a portion within the surface of the substrate A (reference 42) such that the coating solution contacts both of the substrate A (reference 42) and the member B (reference 43).

FIG. 3C is a schematic view showing an aspect in which the dropped coating solution (reference 41) is then slowly dried in a state where the positional relationship between the substrate A (reference 42) and the member B (reference 43) is maintained. The coating solution (reference 41) starts to be dried from both edges where the film thickness is small and is crystallized, and in this way, large-sized crystals can be obtained.

Figure 4A:
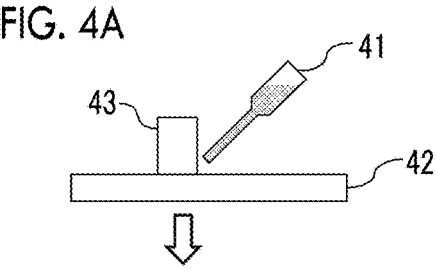
Figure 4A:
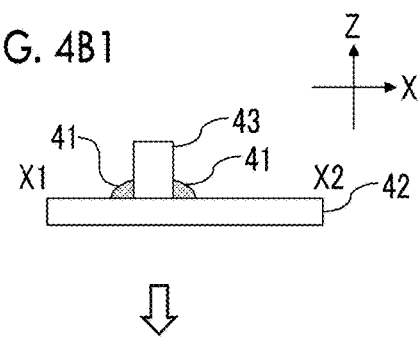
Figure 4A:
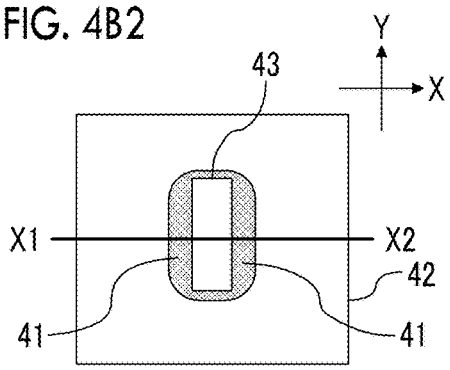
Figure 4C:
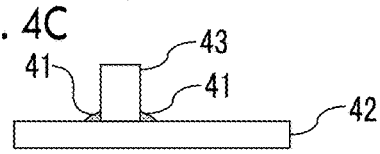

FIGS. 4A to 4C are schematic views showing another example of the method for manufacturing an organic semiconductor film of the present invention.

FIG. 4A shows a state where the coating solution (reference 41) has not yet been dropped onto the substrate A (reference 42). In this state, the substrate A (reference 42) and the member B (reference 43) are caused to remain in contact with each other.

FIG. 4B1 shows a state where the coating solution (reference 41) is then dropped onto a portion within the surface of the substrate A (reference 42) such that the coating solution contacts both of the substrate A (reference 42) and the member B (reference 43). It is FIG. 4B2 that is obtained when FIG. 4B 1 is seen in a vertical direction (Y-axis direction). As is evident from FIG. 4B2, the coating solution (reference 41) is dropped on a portion within the surface of the substrate A (reference 42).

FIG. 4C is a schematic view showing an aspect in which the dropped coating solution (reference 41) is then slowly dried in a state where the positional relationship between the substrate A (reference 42) and the member B (reference 43) is maintained. The coating solution (reference 41) starts to be dried from both edges where the film thickness is small and is crystallized, and in this way, large-sized crystals can be obtained.

Comparing the aspect shown in FIGS. 3A to 3C with the aspect shown in FIGS. 4A to 4C, the aspect shown in FIGS. 4A to 4C in which the substrate A (reference 42) and the member B (reference 43) are caused to remain in contact with each other is preferable, because in this aspect, the film quality is excellent, a holding mechanism is not necessary, and the distance between the member B (reference 43) and the substrate A (reference 42) can be accurately maintained.

Figure 5A:
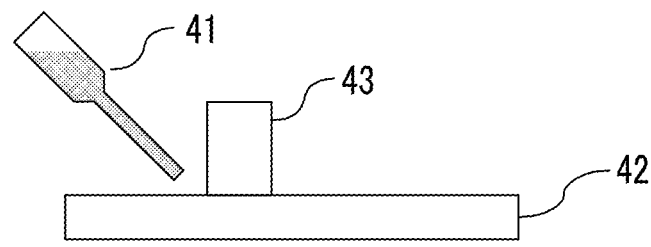
FIGS. 5A to 5C are schematic views showing another example of the method for manufacturing an organic semiconductor film of the present invention. Specifically, FIGS.
Figure 5B:
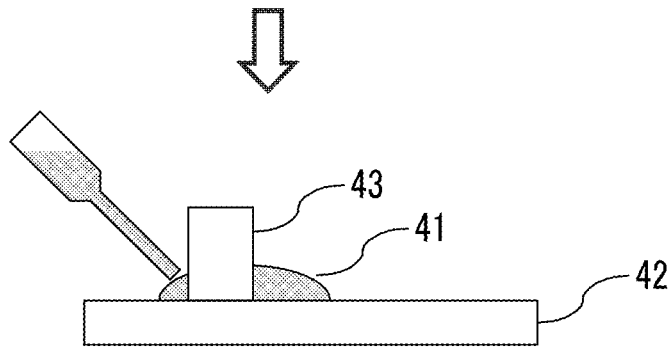
Figure 5C:
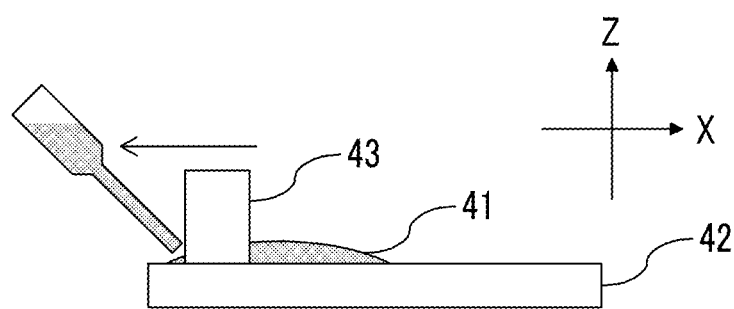

FIGS. 5A to 5C are schematic vies showing another example of the method for manufacturing an organic semiconductor film of the present invention.

FIG. 5A shows a state where the coating solution (reference 41) has not yet been dropped onto the substrate A (reference 42). In this state, the substrate A (reference 42) and the member B (reference 43) are caused to remain in contact with each other.

FIG. 5B shows a state where the coating solution (reference 41) is then dropped onto a portion within the surface of the substrate A (reference 42) such that the coating solution contacts both of the substrate A (reference 42) and the member B (reference 43).

FIG. 5C is a schematic view showing an aspect in which the dropped coating solution is then slowly dried by changing the positional relationship between the substrate A (reference 42) and the member B (reference 43).

In the method for manufacturing an organic semiconductor film of the present invention, as long as the state where the distance between the substrate A and the member B is kept constant or as long as the substrate A and the member B are caused to remain in contact with each other, at the time when the coating solution is dropped or dried, the positional relationship between the substrate A and the member B may be maintained or changed. As shown in FIG. 5C, by changing the positional relationship between the substrate A (reference 42) and the member B (reference 43) in the −X direction on the coordinates, the coating solution (reference 41) starts to be dried from the edge (+X direction on the coordinates) far away from the member B (reference 43) and is crystallized, and in this way, large-sized crystals can be obtained.

Comparing the aspect shown in FIGS. 5A to 5C with the aspect shown in FIGS. 4A to 4C, the aspect shown in FIGS. 4A to 4C is preferable because in this aspect, the film quality is excellent, and large-sized crystals are easily obtained.

Examples of the substrate A used in the method for manufacturing an organic semiconductor film of the present invention include those used as a substrate of the organic transistor of the present invention. As the substrate A, a substrate in which an insulating layer is formed on the substrate of the organic transistor of the present invention is preferable.

The member B used in the method for manufacturing an organic semiconductor film of the present invention is not particularly limited. The material of the member B is preferably glass; quartz; silicon; Teflon (registered trademark); or plastic such as polyethylene or polypropylene, and more preferably glass.

The size of the member B (reference 43) (for example, the length of the member B (reference 43) in the X-axis direction and the Y-axis direction in FIG. 4B2) is not particularly limited. The lower limit of the length of one side of the member B (reference 43) is preferably equal to or greater than 0.1% of the length of one side of the substrate A (reference 42), more preferably equal to or greater than 1% of the length one side of the substrate A, particularly preferably equal to or greater than 10% of the length of one side of the substrate A, and more particularly preferably equal to or greater than 20% of the length of one side of the substrate A. The upper limit of the length of one side of the member B (reference 43) is preferably equal to or less than 80% of the length of one side of the substrate A (reference 42), more preferably equal to or less than 70% of the length of one side of the substrate A, and particularly preferably equal to or less than 50% of the length of one side of the substrate A.

The height of the member B (reference 43) (for example, the length of the member B (reference 43) in the Z-axis direction in FIG. 4B1 is not particularly limited. The height of the member B (reference 43) is preferably 1 mm to 50 mm, and more preferably 5 mm to 20 mm.

FIG. 6 is a schematic view of the substrate A and the member B. In FIG. 6, d indicates the length of the member B in the x-axis direction in FIG. 4B2; w indicates the length of the member B in the y-axis direction in FIG. 4B2; and h indicates the length of the member B in the z-axis direction in FIG. 4B1. h/d in the member B shown in FIG. 6 is preferably 0.01 to 10, and more preferably 0.1 to 5, because then the member B does not collapse. w/d is preferably 1 to 1,000, and more preferably 5 to 100, because then the region in which crystals are formed widens.

(Film Forming Method)

In the method for manufacturing an organic semiconductor film of the present invention, at the time of forming a film, the substrate may be heated or cooled. By varying the temperature of the substrate, it is possible to control the film quality or the packing of molecules in the film. The temperature of the substrate is not particularly limited. However, it is preferably between 0° C. to 200° C., more preferably between 15° C. to 100° C., and particularly preferably between 20° C. to 95° C.

When the compound of the present invention is formed into a film on the substrate, a solution process is used for forming the film.

Herein, the film forming method by a solution process refers to a method of dissolving an organic compound in a solvent which can dissolve the compound and forming a film by using the solution. Specifically, it is possible to use general methods like various printing methods such as a drop casting method, an ink jet method, a screen printing method, a gravure printing method, a flexographic printing method, an offset printing method, and a micro-contact printing method. Among these, an ink jet method, a gravure printing method, a flexographic printing method, an offset printing method, and a micro-contact printing method are preferably used, and a flexographic printing method, a micro-contact printing method, and an ink jet method are particularly preferably used.

In the method for manufacturing an organic semiconductor film of the present invention, the coating solution is dropped onto a portion within the surface of the substrate A such that the coating solution contacts both of the substrate A and the member B.

At the time of dropping the coating solution, it is preferable to drop a single drop of the coating solution or to drop the coating solution drop by drop in a case where two or more drops of the coating solution are dropped, because then a portion in which a film of the coating solution having a small thickness is easily formed on the substrate A, and it is easy to accelerate drying of the coating solution from edge.

In a case where the coating solution is dropped, the volume of a single drop of the coating solution is preferably 0.01 ml to 0.2 ml, and more preferably 0.02 ml to 0.1 ml.

By dropping the coating solution onto a portion within the surface of the substrate A such that the coating solution contacts both of the substrate A and the member B, it is possible to reduce the film thickness at the edge of the coating solution.

The contact angle between the coating solution and the substrate A is preferably 0° to 90°, and more preferably 10° to 80°.

The coating solution and the member B preferably form a meniscus, and more preferably form a concave meniscus from the viewpoint of the film quality.

Usually, in order to form a film by a solution process, the material needs to dissolve in the solvent exemplified above, but simply dissolving in a solvent is not good enough. Generally, even the material formed into a film by a vacuum process can dissolve in a solvent to some extent. The solution process includes a step of coating a substrate with a material by dissolving the material in a solvent and then forming a film by evaporating the solvent, and many of the materials not being suitable for being formed into a film by the solution process have high crystallinity. Therefore, the material is inappropriately crystallized (aggregated) in the aforementioned step, and hence it is difficult to form an excellent film. This problem has been considered in the related art. In contrast, according to the method for manufacturing an organic semiconductor film of the present invention, it is possible to form an organic semiconductor film in a state of causing the precipitation of crystals.

(Drying)

In the method for manufacturing an organic semiconductor film of the present invention, the dropped coating solution is slowly dried so as to cause the precipitation of crystals of the compound of the present invention or the compound represented by Formula (2), thereby forming a semiconductor active layer.

From the viewpoint of the film quality, it is preferable that the coating solution is air-dried on the heated substrate A and then dried under reduced pressure.

The temperature of the substrate A at the time of air drying is preferably 20° C. to 100° C., and more preferably 50° C. to 80° C.

The air drying is preferably performed for 0.5 hours to 20 hours, and more preferably performed for 1 hour to 10 hours.

The temperature at the time of drying under reduced pressure is preferably 20° C. to 100° C., and more preferably 40° C. to 80° C.

The drying under reduced pressure is preferably performed for 1 hour to 20 hours, and more preferably performed for 2 hours to 10 hours.

The pressure at the time of drying under reduced pressure is preferably $10^{-6}$ Pa to $10^{-2}$ Pa, and more preferably $10^{-5}$ Pa to $10^{-3}$ Pa.

In the method for manufacturing an organic semiconductor film of the present invention, crystals of the compound of the present invention or the compound represented by Formula (2) are precipitated. Whether or not the crystals have been precipitated can be checked by observation using a polarizing microscope.

[Organic Semiconductor Material for Non-Light-Emitting Organic Semiconductor Device]

The present invention also relates to an organic semiconductor material for a non-light-emitting organic semiconductor device containing the compound of the present invention.

(Non-Light-Emitting Organic Semiconductor Device)

In the present specification, a "non-light-emitting organic semiconductor device" refers to a device which is not used for the purpose of emitting light. Particularly, a "non-light-emitting organic semiconductor device" refers to a device which is not used for the purpose of emitting visible light. The non-light-emitting organic semiconductor device preferably uses an electronic element having a layered structure consisting of films. The non-light-emitting organic semiconductor device includes an organic transistor, an organic photoelectric conversion element (a solid-state imaging element used for a photosensor, a solar cell used for energy conversion, or the like), a gas sensor, an organic rectifying element, an organic inverter, an information recording element, and the like. The organic photoelectric conversion element can be used for a photosensor (solid-state imaging element) and for energy conversion (a solar cell). Among these, an organic photoelectric conversion element and an organic transistor are preferable, and an organic transistor is more preferable. That is, the organic semiconductor material for a non-light-emitting organic semiconductor device of the present invention is preferably a material for an organic transistor as described above.

(Organic Semiconductor Material)

In the present specification, the "organic semiconductor material" is an organic material showing characteristics of a semiconductor. Just as a semiconductor composed of an inorganic material, the organic semiconductor is classified into a p-type (hole-transporting) organic semiconductor material conducting holes as carriers and an n-type (electron-transporting) organic semiconductor material conducting electrons as carriers.

The compound of the present invention may be used as any of the p-type organic semiconductor material and the n-type organic semiconductor material, but is preferably used as the p-type. The ease with which the carriers flow in the organic semiconductor is represented by a carrier mobility $\mu$. The higher the carrier mobility $\mu$, the better. The carrier mobility $\mu$ is preferably equal to or greater than $1 \times 10^{-2}$ cm$^2$/Vs, more preferably equal to or greater than $1 \times 10^{-1}$ cm$^2$/Vs, particularly preferably equal to or greater than $3 \times 10^{-1}$ cm$^2$/Vs, more particularly preferably equal to or greater than $5 \times 10^{-1}$ cm$^2$/Vs, and even more particularly preferably equal to or greater than 1 cm$^2$/Vs. The carrier mobility $\mu$ can be determined by the characteristics of the prepared field effect transistor (FET) element or by a time-of-flight (TOF) measurement method.

[Organic Semiconductor Film for Non-Light-Emitting Organic Semiconductor Device]

A first aspect of the organic semiconductor film for a non-light-emitting organic semiconductor device of the present invention preferably contains a compound represented by the following Formula (2) and a polymer binder.

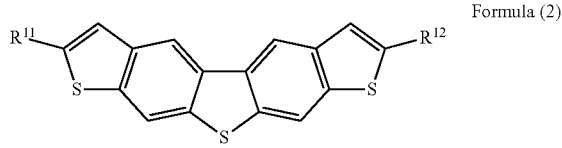

Formula (2)

In Formula (2), $R^{11}$ and $R^{12}$ each independently represent a hydrogen atom, an alkyl group, an alkenyl group, an alkynyl group, or an alkoxy group and may have a substituent, and an aromatic portion in Formula (2) may be substituted with a halogen atom.

A second aspect of the organic semiconductor film for a non-light-emitting organic semiconductor device of the present invention contains the compound of the present invention.

The organic semiconductor film for a non-light-emitting organic semiconductor device of the present invention is preferably manufactured by the method for manufacturing an organic semiconductor film of the present invention.

(Material)

The present invention also relates to the first aspect of the organic semiconductor film for a non-light-emitting organic semiconductor device containing a compound represented by Formula (2), which will be described later, and a polymer binder.

The present invention also relates to the second aspect of the organic semiconductor film for a non-light-emitting organic semiconductor device containing the compound of the present invention.

As the second embodiment of the organic semiconductor film for a non-light-emitting organic semiconductor device of the present invention, an aspect containing the compound of the present invention but does not contain a polymer binder.

Furthermore, the second aspect of the organic semiconductor film for a non-light-emitting organic semiconductor device of the present invention may contain the compound of the present invention and a polymer binder.

Examples of the polymer binder include an insulating polymer such as polystyrene, polycarbonate, polyarylate, polyester, polyamide, polyimide, polyurethane, polysiloxane, polysulfone, polymethyl methacrylate, polymethyl acrylate, cellulose, polyethylene, or polypropylene, a copolymer of these, rubber or a thermoplastic elastomer such as ethylene-propylene rubber, acrylonitrile-butadiene rubber, hydrogenated nitrile rubber, fluoro-rubber, a perfluoro elastomer, a tetrafluoroethylene-propylene copolymer, an ethylene-propylene-diene copolymer, styrene-butadiene rubber, polychloroprene, polyneoprene, butyl rubber, a methyl/phenyl silicone resin, a methyl/phenylvinyl/silicone resin, a methyl/vinyl/silicone resin, a fluorosilicone resin, acryl rubber, ethylene acryl rubber, chlorosulfonated polyethylene, chloropolyethylene, an epichlorohydrin copolymer, a polyisoprene-natural rubber copolymer, polyisoprene rubber, a styrene-isoprene block copolymer, a polyester-urethane copolymer, a polyether-urethane copolymer, a polyether ester thermoplastic elastomer, and polybutadiene rubber, a photoconductive polymer such as polyvinylcarbazole or polysilane, a conductive polymer such as polythiophene, polypyrrole, polyaniline, or poly p-phenylenevinylene, and a semiconductor polymer described in, for example, Chemistry of Materials, 2014, 26, 647.

One kind of polymer binder may be used singly, or plural kinds thereof may be used in combination.

The organic semiconductor material may be uniformly mixed with the polymer binder. Alternatively, the organic semiconductor material and the polymer binder may be totally or partially in a phase separation state. From the viewpoint of the charge mobility, a structure, in which the organic semiconductor and the binder are in a phase separation state along the film thickness direction in the film, is the most preferable because then the binder does not hinder the organic semiconductor from moving a charge.

Considering the mechanical strength of the film, a polymer binder having a high glass transition temperature is preferable. However, for the purpose of imparting flexibility to the film, a polymer binder having a low glass transition temperature is preferable. Considering the charge mobility, a polymer binder having a structure not containing a polar group and a conductive polymer are preferable.

The amount of the polymer binder used is not particularly limited. However, in the organic semiconductor film for a non-light-emitting organic semiconductor device of the present invention, the amount of the polymer binder used is preferably within a range of 0% to 95% by mass, more preferably within a range of 10% to 90% by mass, even more preferably within a range of 20% to 80% by mass, and particularly preferably within a range of 30% to 70% by mass.

In the present invention, because the compound of the present invention or the compound represented by Formula (2) has the aforementioned structure, an organic film having excellent film quality can be obtained. Specifically, the compound of the present invention or the compound represented by Formula (2) has excellent crystallinity, a sufficient film thickness can be obtained, and the obtained organic semiconductor film for a non-light-emitting organic semiconductor device of the present invention has excellent quality.

In a case where the organic semiconductor film for a non-light-emitting organic semiconductor device of the present invention is manufactured by the method for manufacturing an organic semiconductor film of the present invention, the organic semiconductor film becomes an organic film having excellent film quality.

EXAMPLES

Hereinafter, the characteristics of the present invention will be more specifically explained by describing examples and comparative examples. The materials, the amount thereof used, the proportion thereof, the content of treatment, the treatment procedure, and the like described in the following examples can be appropriately modified within a range that does not depart from the gist of the present invention. Accordingly, the scope of the present invention is not limited to the following specific examples.

Example 1

Compounds described in Table 1 or 2 were synthesized.
<Synthesis Method>
A compound 1 having the following structure that was used in the organic transistor of the present invention was synthesized according to the following synthesis method.

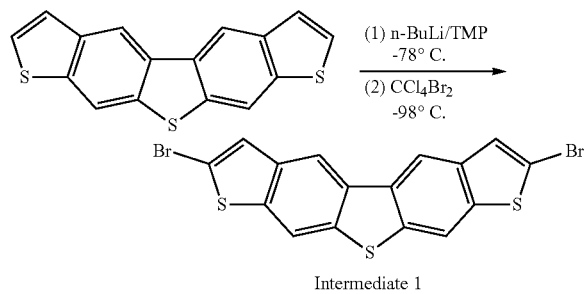

Intermediate 1

(Synthesis of Intermediate 1)

23.1 ml of tetrahydrofuran was added to 3.93 ml of tetramethylpiperidine (TMP), followed by stirring at −78° C., and 13.8 ml of n-butyllithium (1.6 M hexane solution) was added thereto. Then, the mixture was heated to 0° C. and stirred for 1 hour, thereby preparing a lithium reagent.

100 ml of tetrahydrofuran was added to 2.969 g (10 mmol) of thieno[3,2-f:4,5-f′]bis[1]benzothiophene as a known material synthesized according to the synthesis method described in J. Org. Chem. 2005, 70, 4502, followed by stirring at −78° C., and the aforementioned lithium reagent was added dropwise thereto at −78° C. by using a cannula. After 2 hours, the reaction solution was cooled to −98° C., and a solution obtained by dissolving 9.76 g (30 mmol) of dibromodichloroethane in 30 ml of tetrahydrofuran was added dropwise thereto by using a cannula. Then, the reaction solution was slowly heated to room temperature from −98° C. and stirred for 15 hours. After the reaction solution was cooled to 0° C., water was added thereto, and the precipitate was separated by filtration. The solid separated by filtration was recrystallized from 1,1,2,2-tetrachloroethane, thereby obtaining 3.95 g (8.70 mmol) of a target compound (intermediate 1) in the form of solid with light orange color. The obtained compound was identified by Nuclear Magnetic Resonance ($^1$H-NMR).

$^1$H-NMR (tetrachloroethane-$d_2$, 400 MHz) δ: 7.46 (2H, s), 8.12 (2H, s), 8.45 (2H, s)

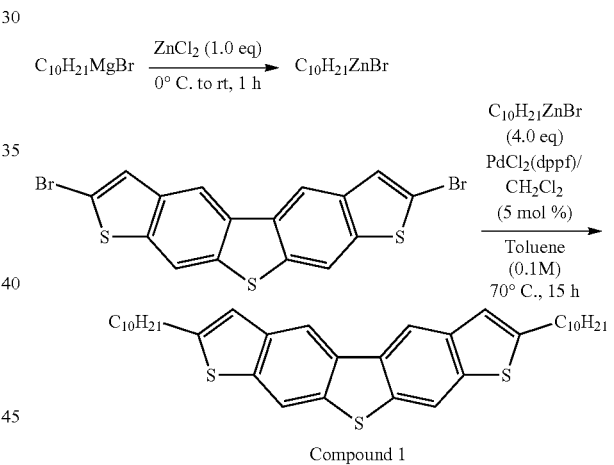

Compound 1

(Synthesis of Compound 1)

4.8 ml (4.80 mmol) of decyl magnesium bromide (1.0 mol/L diethylether solution) was added to the intermediate 1 and cooled to 0° C. At this point in time, 4.8 ml (4.80 mmol) of zinc (II) chloride (1.0 mol/L tetrahydrofuran solution) was added dropwise thereto, thereby preparing an organic zinc reagent. The organic zinc reagent was added to a system to which 545 mg (1.20 mmol) of the intermediate 1, 49 mg (0.06 mmol) of [1,1′-bis(diphenylphosphino)ferrocene]dichloropalladium (II), and 12 ml of toluene were added, followed by stirring for 20 minutes at room temperature. Then, the reaction solution was heated to 70° C. and stirred for 15 hours. After the reaction ended, the reaction solution was cooled to room temperature, 50 ml of methanol was added thereto, and the precipitated solid was separated by filtration. The solid was dissolved in heated O-dichlorobenzene, passed through celite and silica gel in the heated state, and eluted using O-dichlorobenzene. The solution was concentrated using an evaporator and then recrystallized from heated O-dichlorobenzene, thereby obtaining 440 mg (0.763 mmol) of a target compound 1 in the form of white solid.

The structure of the compound 1 was identified by $^1$H-NMR. The results are shown below.

$^1$H-NMR (tetrachloroethane-d$_2$, 400 MHz) δ: 0.82 (6H, t, J=7.2 Hz), 1.21-1.37 (28H, m), 1.71 (4H, quin, J=7.4 Hz), 2.88 (4H, t, J=7.6 Hz), 7.09 (2H, s), 8.11 (2H, s), 8.39 (2H, s)

Synthesis of Compound 4 (Synthesis Method and NMR)

A compound 4 was synthesized in the same manner as used for synthesizing the compound 1, except that decyl magnesium bromide (1.0 M diethylether solution) was changed to butyl magnesium chloride (1.0 M tetrahydrofuran solution).

The structure of the compound 4 was identified by $^1$H-NMR. The results are shown below.

$^1$H-NMR (CDCl$_3$, 400 MHz) δ: 0.98 (6H, t, 7.2 Hz), 1.41-1.50 (4H, m), 1.72-1.81 (4H, m), 2.94 (4H, t, 7.0 Hz), 7.13 (2H, s), 8.15 (2H, s), 8.44 (2H, s) ppm.

Synthesis of Compound 5

A compound 5 was synthesized in the same manner as used for synthesizing the compound 1, except that decyl magnesium bromide (1.0 M diethylether solution) was changed to pentyl magnesium bromide (1.0 M tetrahydrofuran solution).

The structure of the compound 5 was identified by $^1$H-NMR. The results are shown below.

$^1$H-NMR (CDCl$_3$, 400 MHz) δ: 0.93 (6H, t, 7.3 Hz), 1.37-1.55 (8H, m), 1.75-1.83 (4H, m), 2.94 (t, 7.0 Hz), 7.13 (2H, s), 8.15 (2H, s), 8.44 (2H, s) ppm.

A compound 6 was synthesized according to Tetrahedron 66 (2010) 8778-8784.

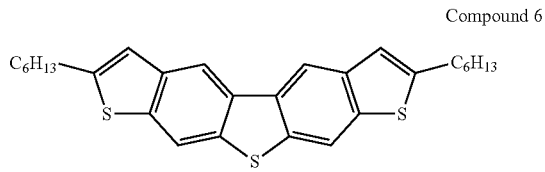

Compound 6

Synthesis of Compound 11

A compound 11 was synthesized in the same manner as used for synthesizing the compound 1, except that decyl magnesium bromide (1.0 M diethylether solution) was changed to 6-methyloctyl bromide (1.0 M tetrahydrofuran solution).

The structure of the compound 11 was identified by $^1$H-NMR. The results are shown below.

$^1$H-NMR (CDCl$_3$, 400 MHz) δ: 0.84-0.88 (12H, m), 1.08-1.17 (4H, m), 1.30-1.44 (14H, m), 1.75-1.83 (4H, m), 2.94 (4H, t, 7.1 Hz), 7.13 (2H, s), 8.15 (2H, s), 8.44 (2H, s) ppm.

Synthesis of Compound 18 (Synthesis Method and NMR)

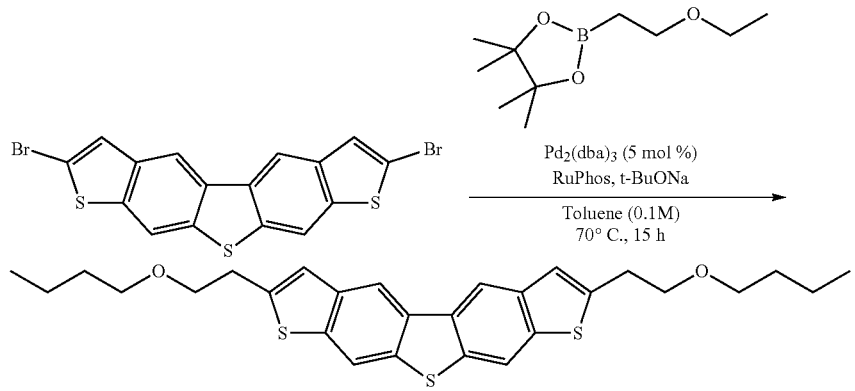

The intermediate 1 (300 mg, 0.66 mmol), 2-(2-butoxyethyl)-4,4,5,5-tetramethyl-1,3,2-dioxabolane (452 mg, 1.98 mmol), tris(dibenzylideneacetone)dipalladium (0) (Pd$_2$(dba)$_3$) (30 mg, 0.033 mmol), 2-dicyclohexylphosphino-2',6'-diisopropoxybiphenyl (RuPhos) (61 mg, 0.132 mmol), t-butoxysodium (381 mg, 4.00 mmol), 7 mL of toluene, and 7 mL of pure water were mixed together, followed by stirring for 2.5 hours at 80° C. The reaction solution was cooled to room temperature and subjected to liquid separation by using chloroform and pure water. An organic layer was concentrated through distillation under reduced pressure and then purified by column chromatography (sequential development using silica gel, hexane:ethyl acetate=3:1, hexane:ethyl acetate=2:1, and hexane:ethyl acetate=1:1), thereby obtaining 140 mg (0.282 mmol) of a compound 18 as a white solid.

The obtained compound was identified by $^1$H-NMR.

$^1$H-NMR (CDCl$_3$, 400 MHz) δ: 0.94 (6H, t, 7.3 Hz), 1.36-1.46 (4H, m), 1.58-1.65 (4H, m), 3.20 (4H, t, 7.1 Hz), 3.51 (4H, t, 7.0 Hz), 3.51 (4H, t, 7.0 Hz), 3.77 (4H, t, 7.2 Hz), 7.20 (2H, s), 8.15 (2H, s), 8.46 (2H, s) ppm.

Synthesis of Compound 20

A compound 20 was synthesized in the same manner as used for synthesizing the compound 1, except that decyl magnesium bromide (1.0 M diethylether solution) was changed to 4-butoxybutyl magnesium bromide (1.0 M THF solution).

The structure of the compound 20 was identified by $^1$H-NMR. The results are shown below.

$^1$H-NMR (CDCl$_3$, 400 MHz) δ: 0.93 (6H, t, 7.4 Hz), 1.34-1.43 (4H, m), 1.53-1.60 (4H, m), 1.68-1.75 (4H, m), 1.83-1.91 (4H, m), 2.97 (4H, t, 7.3 Hz), 3.42 (4H, t, 7.0 Hz), 3.47 (4H, t, 7.0 Hz) ppm.

Synthesis of Compound 29

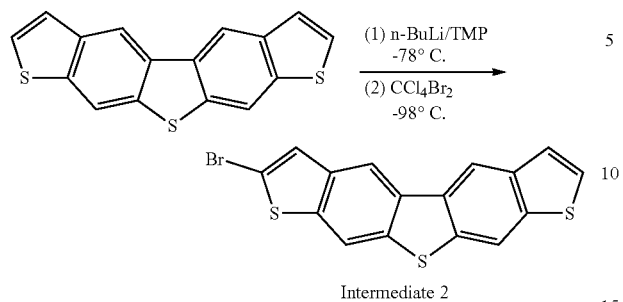

Intermediate 2

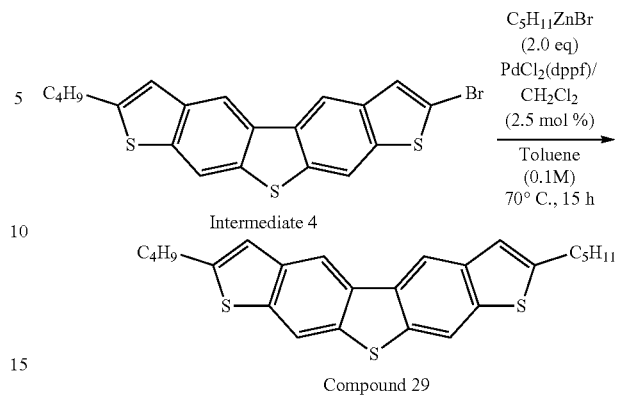

Intermediate 4

Compound 29

(Synthesis of Intermediate 2)

An intermediate 2 was synthesized in the same manner as used for synthesizing the intermediate 1, except that the amounts of all of the tetramethylpiperidine (TMP), n-butyllithium, and dibromodichloroethane were halved.

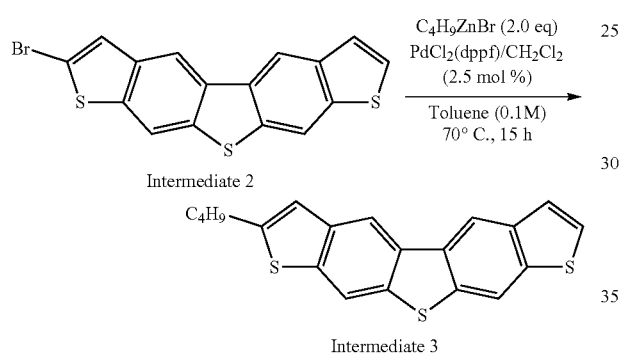

Intermediate 2

Intermediate 3

(Synthesis of Intermediate 3)

An intermediate 3 was synthesized in the same manner as used for synthesizing the compound 4, except that the intermediate 1 was changed to the intermediate 2, and the equivalents of organic zinc reagent and [1,1'-bis(diphenylphosphino)ferrocene]dichloropalladium (II) were halved.

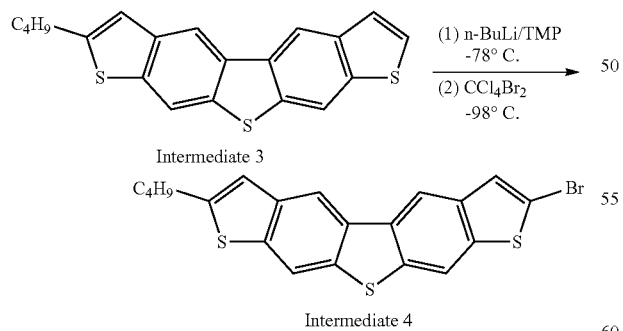

Intermediate 3

Intermediate 4

(Synthesis of Intermediate 4)

An intermediate 4 was synthesized in the same manner as used for synthesizing the intermediate 2, except that the intermediate 3 was used instead of thieno[3,2-f:4,5-f']bis[1]benzothiophene.

A compound 29 was synthesized in the same manner as used for synthesizing the compound 5, except that the intermediate 1 was changed to the intermediate 4, and the equivalents of organic zinc reagent and [1,1'-bis(diphenylphosphino)ferrocene]dichloropalladium (II) were halved.

The structure of the compound 29 was identified by $^1$H-NMR. The results are shown below.

$^1$H-NMR (CDCl$_3$, 400 MHz) δ: 0.92 (3H, t, 7.2 Hz), 0.98 (3H, t, 7.2 Hz), 1.38-1.52 (6H, m), 1.73-1.82 (4H, m), 2.92-2.97 (4H, m), 7.13 (2H, s), 8.15 (2H, s), 8.44 (2H, s) ppm.

[Synthesis of Comparative Compound]

A comparative compound 1 having the following structure was synthesized according to the synthesis method described in J. Org. Chem. 2005, 70, 4502.

Comparative compound 1

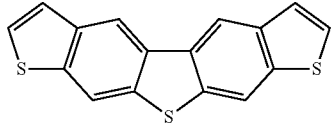

The following comparative compounds 2 to 6 were synthesized with reference to JP2013-235903A, CN102206225A, and WO2011/126225A, JP2009-302463A, and JP2010-177642A respectively. The comparative compounds 2 and 3 were measured by gel permeation chromatography (GPC), and as a result, it was confirmed that they have a weight-average molecular weight (Mw) of 40,000.

Comparative compound 2

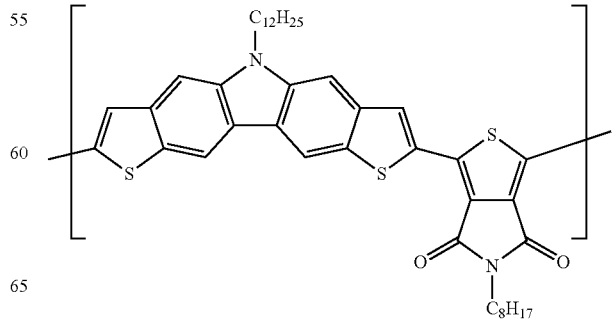

-continued

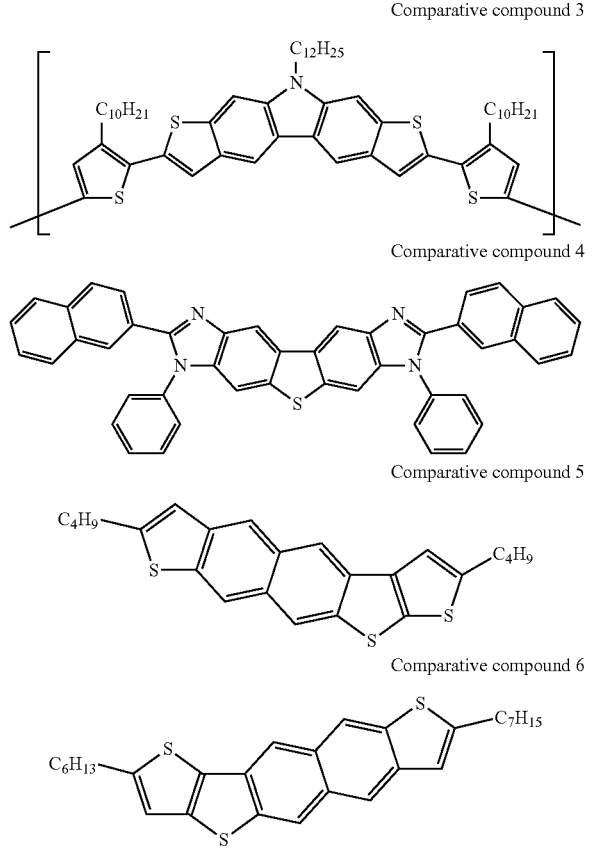

Comparative compound 3

Comparative compound 4

Comparative compound 5

Comparative compound 6

Examples 1-1 to 1-8 and Comparative Elements 1-1 to 1-4

<Preparation/Evaluation of Element>

Through high-performance liquid chromatography, it was confirmed that the materials used for preparing elements had purity (area ratio for absorption intensity at 254 nm) of equal to or higher than 99.0%.

A semiconductor active layer (organic semiconductor film) was formed using a compound alone.

Any one of compounds or comparative compounds 1 to 4 described in the following table was prepared into a 0.1% by mass solution by being dissolved in anisole as a solvent and then heated to 50° C. The solution was used as a coating solution for an organic semiconductor device (referred to as a coating solution as well).

In the elements 1-1 to 1-8 and the comparative elements 1-1 to 1-4, an organic semiconductor film was formed by the method shown in FIGS. 4A to 4C. Herein, "1-1 to 1-8" means 1-1, 1-2, 1-3, 1-4, 1-5, 1-6, 1-7, and 1-8. The same will be also applied in a case where branch numbers are described using "to". Specifically, the organic semiconductor film was formed as below.

A 25 mm×25 mm substrate prepared by forming a thermally oxidized SiO$_2$ film having a thickness of 200 nm on the surface of an n-type silicon substrate (thickness: 0.4 mm) was used as a substrate A. The surface of the thermally oxidized film of the substrate A was cleaned with ultraviolet (UV)-ozone and then treated with β-phenethyltrimethoxysilane.

On the surface of the substrate A treated with β-phenethyltrimethoxysilane, a member B was placed on the central portion of the substrate A as shown in FIG. 4A such that the substrate A and the member B contacted each other. As the member B, a substance made of glass and having a size of 10 mm (length)×2 mm (width)×5 mm (height) was used. The transverse direction (X-axis direction) in FIG. 4A is the width direction of the member B; the vertical direction (Z-axis direction) in FIG. 4A is the height direction of the member B; and the vertical direction (Y-axis direction) in FIG. 4B2 is the longitudinal direction of the member B.

The substrate was heated to 50° C., and one drop (about 0.05 ml) of the coating solution prepared by the method described above was placed onto the substrate by using a pipette from the lateral side of the member B such that the drop contacted both of the substrate A and the member B as shown in FIG. 4A. As a result, as shown in FIGS. 4B1 and 4B2, the coating solution was dropped onto a portion within the surface of the substrate A. In the interface between the coating solution and the substrate B, a concave meniscus was formed.

As shown in FIG. 4C, in a state where the substrate A and the member B were caused to remain in contact with each other, and the positional relationship between the substrate A and the member B were maintained, the coating solution was air-dried. Then, the coating solution was dried under reduced pressure for 8 hours at 60° C. at a pressure of $10^{-3}$ MPa such that crystals of any one of the compounds or comparative compounds 1 to 4 described in the following table were precipitated, thereby forming an organic semiconductor film. Whether or not crystals were precipitated was checked by observation using a polarizing microscope.

The obtained organic semiconductor film was used as a semiconductor active layer and covered with a mask. Then, F4-TCNQ with a thickness of 1 nm as a charge injection acceptor and a gold electrode with a thickness of 40 nm were vapor-deposited thereon, thereby obtaining a bottom gate/top contact-type organic transistor element for measuring FET characteristics. The obtained organic transistor element was taken as the elements 1-1 to 1-8 and the comparative elements 1-1 to 1-4. The elements 1-1 to 1-8 and the comparative elements 1-1 to 1-4 were taken as organic transistor elements of Examples 1-1 to 1-8 and Comparative examples 1 to 4.

<Evaluation>

By using a semiconductor parameter analyzer (4156C manufactured by Agilent Technologies) connected to a semi-automatic prober (AX-2000 manufactured by Vector Semiconductor Co., Ltd.), the FET characteristics of the organic transistor elements as the elements 1-1 to 1-8 and the comparative elements 1-1 to 1-4 were evaluated under a normal pressure/atmosphere.

The obtained results are shown in the following Table 3.

(a) Carrier Mobility

Between the source electrode and the drain electrode of each organic film transistor element (FET element), a voltage of −80 V was applied, and the gate voltage was varied within a range of 20 V to −100 V. In this way, a carrier mobility μ was calculated using the following equation showing a drain current $I_d$.

$$I_d = (w/2L)\mu C_i(V_g - V_{th})^2$$

(In the equation, L represents a gate length, W represents a gate width, $C_i$ represents a capacity of the insulating layer per unit area, $V_g$ represents a gate voltage, and $V_{th}$ represents a threshold voltage.)

TABLE 3

| Element No. | Organic semiconductor material | Carrier mobility (cm$^2$/Vs) | Note |
|---|---|---|---|
| Element 1-1 | Compound 1 | 6.0 | Present invention |
| Element 1-2 | Compound 4 | 2.9 | Present invention |
| Element 1-3 | Compound 6 | 1.0 | Present invention |
| Element 1-4 | Compound 21 | 1.5 | Present invention |
| Element 1-5 | Compound 24 | 2.1 | Present invention |
| Element 1-6 | Compound 33 | 1.3 | Present invention |
| Element 1-7 | Compound 37 | 1.8 | Present invention |
| Element 1-8 | Compound 40 | 1.6 | Present invention |
| Comparative element 1-1 | Comparative compound 1 | 0.1 | Comparative Example |
| Comparative element 1-2 | Comparative compound 2 | 0.01 | Comparative Example |
| Comparative element 1-3 | Comparative compound 3 | 0.02 | Comparative Example |
| Comparative element 1-4 | Comparative compound 4 | 0.006 | Comparative Example |

From the above Table 3, it was understood that the organic transistor elements as the elements 1-1 to 1-8 of the present invention have high carrier mobility and can be preferably used as organic semiconductor materials.

In contrast, it was understood that the organic transistor elements as the comparative elements 1-1 to 1-4 in which the comparative compounds 1 to 4 were used as organic semiconductor materials in the semiconductor active layer have low carrier mobility.

Examples 2-1 to 2-14 and Comparative Examples 2-1 to 2-3

In Examples 2-1 to 2-14 and Comparative Examples 2-1 to 2-3, a bottom gate/bottom contact-type organic transistor element was prepared. The details are described below.

An anisol solution containing 0.1% by mass of the compound 1 was heated to 100° C. and used as a coating solution for an organic semiconductor device. In a nitrogen atmosphere, the solution was cast onto a substrate for measuring FET characteristics heated to 90° C., thereby obtaining a non-light-emitting organic transistor element 2-1. As the substrate for measuring FET characteristics, a silicon substrate having a bottom gate/bottom contact structure was used which included chromium/gold (gate width W=100 mm, gate length L=100 µm) arranged to form a comb pattern as source and drain electrodes and included SiO$_2$ (film thickness: 200 nm) as an insulating layer. The obtained organic transistor element was taken as an element 2-1. The element 2-1 was taken as an organic transistor element of Example 2-1.

Elements 2-2 to 2-14 and comparative elements 2-1 to 2-3 were prepared in the same manner as used for preparing the element 2-1, except that, in preparing the organic transistor element as the element 2-1, any one of the compounds or comparative compounds described in Table 2 was used instead of the compound 1. The element 2-6 was obtained by mixing the compound 4 and the compound 5 together such that the concentration of each of the compounds became 0.05% by mass.

<Evaluation>

For the elements 2-2 to 2-14 and the comparative elements 2-1 to 2-3, FET characteristics of an organic transistor element were evaluated in the same manner as in Example 1-1. The results are shown in the following Table 4.

TABLE 4

| Element No. | Organic semiconductor material | Carrier mobility (cm$^2$/Vs) | Note |
|---|---|---|---|
| Element 2-1 | Compound 1 | 0.50 | Present invention |
| Element 2-2 | Compound 2 | 0.77 | Present invention |
| Element 2-3 | Compound 3 | 0.52 | Present invention |
| Element 2-4 | Compound 4 | 0.95 | Present invention |
| Element 2-5 | Compound 5 | 0.52 | Present invention |
| Element 2-6 | Compound 4/compound 5 | 0.71 | Present invention |
| Element 2-7 | Compound 6 | 0.30 | Present invention |
| Element 2-8 | Compound 10 | 0.14 | Present invention |
| Element 2-9 | Compound 26 | 0.31 | Present invention |
| Element 2-10 | Compound 28 | 0.64 | Present invention |
| Element 2-11 | Compound 29 | 0.33 | Present invention |
| Element 2-12 | Compound 30 | 0.45 | Present invention |
| Element 2-13 | Compound 32 | 0.42 | Present invention |
| Element 2-14 | Compound 40 | 0.32 | Present invention |
| Comparative element 2-1 | Comparative compound 1 | 0.03 | Comparative Example |
| Comparative element 2-2 | Comparative compound 2 | <0.001 | Comparative Example |
| Comparative element 2-3 | Comparative compound 6 | 0.01 | Comparative Example |

From the above Table 4, it was understood that the organic transistor elements as the elements 2-2 to 2-14 of the present invention have high carrier mobility and can be preferably used as organic semiconductor materials.

In contrast, it was understood that the organic transistor elements as the comparative elements 2-1 to 2-3 in which the comparative compounds 1, 2, and 6 were used as organic semiconductor materials in a semiconductor active layer have low carrier mobility.

Examples 3-1 to 3-29 and Comparative Examples 3-1 to 3-5

Al to be a gate electrode was vapor-deposited (thickness: 50 nm) onto a glass substrate (Eagle XG: manufactured by Corning Incorporated). Onto the Al, a composition for forming a gate insulating film (a propylene glycol monomethyl ether acetate (PGMEA) solution (concentration of solid contents: 2% by mass) containing polyvinylphenol/melamine=1 part by mass/1 part by mass) was applied by spin coating, followed by baking for 60 minutes at 150° C., thereby forming a gate insulating film having a film thickness of 400 nm. On the gate insulating film, by using a silver ink (H-1, manufactured by Mitsubishi Materials Corporation) and an ink jet device DMP-2831 (manufactured by FUJIFILM Dimatix Inc.), patterns of a source electrode and a drain electrode (channel length: 40 µm, channel width: 200 µm) were drawn. Then, the resultant was sintered by being baked for 30 minutes at 180° C. in an oven such that source and drain electrodes were formed, thereby obtaining an element substrate for evaluating thin film transistor (TFT) characteristics.

Onto the element substrate for evaluating TFT characteristics, each of the coating solutions for an organic semiconductor device (an organic semiconductor material (0.50% by mass), a polymer (0.025% by mass), and toluene) described in the following Table 5 was applied by drop casting, and then the element substrate was dried for 10 minutes at 100° C. on a hot plate such that an organic semiconductor layer was formed, thereby obtaining a bottom gate/bottom contact-type organic transistor element. The obtained organic transistor element was taken as elements 3-1 to 3-29 and comparative elements 3-1 to 3-5. The elements 3-1 to 3-29 and the comparative elements 3-1 to 3-5 were taken as organic transistor elements of Examples 3-1 to 3-29 and Comparative elements 3-1 to 3-5. In the following table, F8T2 represents [Poly[(9,9-dioctyl-9H-fluorene-2,7-diyl)-alt-2,2'-bithiophene]-5,5'-diyl)]] (manufactured by Sigma-Aldrich Co., LLC., Mn>20,000); PMMA represents Polymethyl methacrylate (manufactured by Sigma-Aldrich Co., LLC., Mw~15,000); PαMS represents Poly(α-methylstyrene) (manufactured by Sigma-Aldrich Co., LLC., Mw=43,700); and PS represents Polystyrene (manufactured by Sigma-Aldrich Co., LLC., Mw=2,000,000).

<Evaluation>

For the elements 3-1 to 3-29 and the comparative elements 3-1 to 3-5, the FET characteristics of an organic transistor element were evaluated in the same manner as in Example 1. The results are shown in the following Table 5.

TABLE 5

| Element No. | Organic semiconductor material | Polymer (binder) | Carrier mobility (cm$^2$/Vs) | Note |
|---|---|---|---|---|
| Element 3-1 | Compound 4 | F8T2 | 0.35 | Present invention |
| Element 3-2 | Compound 7 | — | 0.27 | Present invention |
| Element 3-3 | Compound 8 | — | 0.11 | Present invention |
| Element 3-4 | Compound 9 | — | 0.31 | Present invention |
| Element 3-5 | Compound 11 | PMMA | 0.01 | Present invention |
| Element 3-6 | Compound 12 | — | 0.01 | Present invention |
| Element 3-7 | Compound 13 | — | 0.02 | Present invention |
| Element 3-8 | Compound 14 | — | 0.05 | Present invention |
| Element 3-9 | Compound 15 | — | 0.01 | Present invention |
| Element 3-10 | Compound 16 | — | 0.01 | Present invention |
| Element 3-11 | Compound 17 | — | 0.01 | Present invention |
| Element 3-12 | Compound 17 | PαMS | 0.01 | Present invention |
| Element 3-13 | Compound 18 | — | 0.02 | Present invention |
| Element 3-14 | Compound 19 | — | 0.05 | Present invention |
| Element 3-15 | Compound 20 | — | 0.05 | Present invention |
| Element 3-16 | Compound 21 | — | 0.03 | Present invention |
| Element 3-17 | Compound 22 | — | 0.01 | Present invention |
| Element 3-18 | Compound 23 | — | 0.01 | Present invention |
| Element 3-19 | Compound 24 | — | 0.01 | Present invention |
| Element 3-20 | Compound 25 | — | 0.31 | Present invention |
| Element 3-21 | Compound 27 | — | 0.30 | Present invention |
| Element 3-22 | Compound 31 | — | 0.20 | Present invention |
| Element 3-23 | Compound 33 | — | 0.23 | Present invention |
| Element 3-24 | Compound 34 | PαMS | 0.02 | Present invention |
| Element 3-25 | Compound 35 | — | 0.01 | Present invention |
| Element 3-26 | Compound 36 | — | 0.02 | Present invention |
| Element 3-27 | Compound 37 | — | 0.02 | Present invention |
| Element 3-28 | Compound 38 | — | 0.04 | Present invention |
| Element 3-29 | Compound 39 | PS | 0.01 | Present invention |
| Comparative element 3-1 | Comparative compound 1 | — | 0.002 | Comparative Example |
| Comparative element 3-2 | Comparative compound 2 | — | <0.001 | Comparative Example |
| Comparative element 3-3 | Comparative compound 4 | — | <0.001 | Comparative Example |
| Comparative element 3-4 | Comparative compound 5 | — | <0.001 | Comparative Example |
| Comparative element 3-5 | Comparative compound 6 | — | <0.001 | Comparative Example |

From the above Table 5, it was understood that the organic transistor elements as the elements 3-1 to 3-29 of the present invention have high carrier mobility and can be preferably used as organic semiconductor materials.

In contrast, it was understood that the organic transistor elements as the comparative elements 3-1 to 3-5 in which the comparative compounds 1, 2, and 4 to 6 were used as organic semiconductor materials in a semiconductor active layer have low carrier mobility.

Examples 4-2 to 4-4 and 4-6 to 4-8

<Preparation Example of TFT Element by Printing Method>

—Ink Jet Method—

The element substrate for evaluating TFT characteristics manufactured in Example 3-1 was coated with a coating solution for an organic semiconductor device (the organic semiconductor compound, the polymer (binder), the solvent, and the concentration described in Table 6) by an ink jet method, thereby forming an organic semiconductor film and obtaining an organic transistor element. By using DPP 2831 (manufactured by FUJIFILM Graphic Systems, Inc.) as an ink jet device and a 10 pL head, a solid film was formed at a jetting frequency of 2 Hz and a dot pitch of 20 μm. The film was then dried for 1 hour at 70° C., thereby preparing an organic semiconductor layer.

—Flexographic Printing Method—

By a flexographic printing method, the element substrate for evaluating TFT characteristics manufactured in Example 3-1 was coated with a coating solution for an organic semiconductor device (the organic semiconductor compound, the polymer (binder), the solvent, and the concentration described in Table 6 and 0.05% by mass of BYK-323 (manufactured by BYK Additives & Instruments) as a surfactant), thereby forming an organic semiconductor film and obtaining an organic transistor element. As a printing device, a flexographic printing suitability tester F1 (manufactured by IGT Testing Systems) was used, and as a resin plate for flexographic printing, AFP DSH 1.70% (manufactured by Asahi Kasei Corporation.)/solid image was used. Under a pressure of 60 N applied between the resin plate for flexographic printing and the element substrate for evaluating TFT characteristics, printing was performed at a transport rate of 0.4 m/sec, and then the substrate was dried as it is for 2 hours at room temperature lower than 40° C., thereby preparing an organic semiconductor layer and obtaining a bottom gate/bottom contact-type organic transistor element.

The obtained organic transistor element was taken as elements 4-2 to 4-4 and 4-6 to 4-8. The elements 4-2 to 4-4 and 4-6 to 4-8 were taken as organic transistor elements of Examples 4-2 to 4-4 and 4-6 to 4-8. Herein, all of those used as an ink in the elements 4-6 to 4-8 had a viscosity of equal to or greater than 10 mPa·s.

TABLE 6

| Element No. | Organic semiconductor | Polymer (binder) | Solvent | Concentration Organic semiconductor/ polymer (wt %) | Printing method | Carrier mobility (cm$^2$/Vs) | Note |
|---|---|---|---|---|---|---|---|
| Element 4-2 | Compound 5 | — | Tetralin | 0.4 | Ink jet | 0.65 | Example |
| Element 4-3 | Compound 17 | — | Toluene | 0.5 | Ink jet | 0.13 | Example |
| Element 4-4 | Compound 31 | PMMA | Mesitylene | 1.0 | Ink jet | 0.35 | Example |
| Element 4-6 | Compound 4 | PαMS | Tetralin | 0.4/1.0 | Flexography | 0.20 | Example |
| Element 4-7 | Compound 29 | PS | Tetralin | 0.5/1.0 | Flexography | 0.25 | Example |
| Element 4-8 | Compound 38 | PαMS | Tetralin | 1.5/1.0 | Flexography | 0.12 | Example |

As shown in Table 6, even in a case where a film was formed by an ink jet method or a flexographic printing method, an organic transistor element having excellent characteristics that has high carrier mobility and can be preferably used as an organic semiconductor material was obtained.

EXPLANATION OF REFERENCES

11: substrate
12: electrode
13: insulator layer
14: semiconductor active layer (organic substance layer, organic semiconductor layer)
15a, 15b: electrode
31: substrate
32: electrode
33: insulator layer
34a, 34b: electrode
35: semiconductor active layer (organic substance layer, organic semiconductor layer)
41: coating solution
42: substrate A
43: member B

What is claimed is:

1. A compound which is represented by the following Formula (2A);

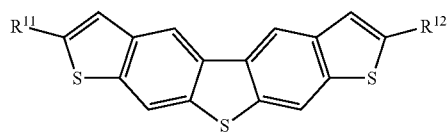

Formula (2A)

in Formula (2A), R$^{11}$ and R$^{12}$ each independently represent a halogen atom, and an aromatic portion in Formula (2A) may be substituted with a halogen atom.

2. The compound according to claim 1, wherein the compound represented by Formula (2A) is an intermediate of a compound which is represented by the following Formula (2), wherein in Formula (2), R$^{11}$ and R$^{12}$ each independently have 3 to 30 carbon atoms in total and represent an alkenyl group, an alkynyl group or an alkoxy group and may have a substituent, or the compound represented by Formula (2) satisfies the following condition A, B, C, or D;

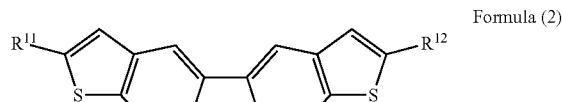

Formula (2)

in Formula (2), an aromatic portion in Formula (2) may be substituted with a halogen atom;

condition A: in Formula (2), R$^{11}$ and R$^{12}$ each independently have 3 to 30 carbon atoms in total and represent an unsubstituted linear alkyl group having an even number of carbon atoms within a range of 8 to 10 carbon atoms, an unsubstituted linear alkyl group having an odd number of carbon atoms within a range of 3 to 15 carbon atoms, a substituted linear alkyl group having 3 to 15 carbon atoms, or a substituted or unsubstituted branched alkyl group having 3 to 18 carbon atoms;

condition B: in Formula (2), R$^{11}$ and R$^{12}$ each independently have 3 to 30 carbon atoms in total and represent an unsubstituted linear alkyl group having an even number of carbon atoms within a range of 2 to 4 carbon atoms;

condition C: in Formula (2), R$^{11}$ and R$^{12}$ each independently have 3 to 30 carbon atoms in total and represent a substituted alkyl group having 1 or 2 carbon atoms;

condition D: in Formula (2), R$^{11}$ and R$^{12}$ each independently have 3 to 30 carbon atoms in total, and R$^{11}$ and R$^{12}$ have different structures.

* * * * *